United States Patent
Asano et al.

(10) Patent No.: US 10,520,429 B2
(45) Date of Patent: Dec. 31, 2019

(54) IMAGE PROCESSING DEVICE, IMAGE PROCESSING METHOD AND IMAGE PROCESSING PROGRAM

(71) Applicant: KONICA MINOLTA, INC., Chiyoda-ku (JP)

(72) Inventors: Motohiro Asano, Osaka (JP); Takashi Morimoto, Suita (JP); Rui Watanabe, Sumoto (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/162,963

(22) Filed: Oct. 17, 2018

(65) Prior Publication Data

US 2019/0049371 A1   Feb. 14, 2019

Related U.S. Application Data

(63) Continuation of application No. 15/770,273, filed as application No. PCT/JP2016/080968 on Oct. 19, 2016, now Pat. No. 10,145,788.

(30) Foreign Application Priority Data

Oct. 29, 2015   (JP) .................. 2015-212518

(51) Int. Cl.
  *G01N 21/25*   (2006.01)
  *G06T 5/50*   (2006.01)
  *G01N 21/3504*   (2014.01)
  *G06T 5/10*   (2006.01)

(52) U.S. Cl.
  CPC .......... *G01N 21/3504* (2013.01); *G06T 5/10* (2013.01); *G06T 5/50* (2013.01); *G06T 2207/10048* (2013.01)

(58) Field of Classification Search
  CPC ...... G01M 3/04; G01M 3/38; G01N 21/3504; G01N 2021/3531; G06T 5/10; G06T 5/50; G06T 7/0004; G06T 2207/10016; G06T 2207/10048; G06T 2207/20056
  See application file for complete search history.

(56) References Cited

U.S. PATENT DOCUMENTS

| 8,242,445 B1 | 8/2012 | Scanlon |
| 2006/0220888 A1 | 10/2006 | Germouni |
| 2009/0200466 A1 | 8/2009 | Mammen et al. |

(Continued)

FOREIGN PATENT DOCUMENTS

| JP | 2012-58093 | 3/2012 |
| JP | 2013-122389 | 6/2013 |

OTHER PUBLICATIONS

Partial supplementary Search Report dated Oct. 15, 2018 issued in the corresponding European Patent Application No. 16859660.9.

(Continued)

*Primary Examiner* — Mark R Gaworecki
(74) *Attorney, Agent, or Firm* — Cozen O'Connor

(57) ABSTRACT

An image processing device performing image processing on images obtained by shooting an object to be monitored at a plurality of time points. The image processing device includes a hardware processor that performs a process of removing, from image data indicating the images, second frequency component data that is lower in frequency than first frequency component data indicating a luminance of the object to be monitored, the second frequency component data indicating a background luminance change of the object to be monitored.

19 Claims, 37 Drawing Sheets

(56) References Cited

U.S. PATENT DOCUMENTS

| | | |
|---|---|---|
| 2011/0185791 A1 | 8/2011 | van Staden |
| 2013/0050466 A1 | 2/2013 | Cetin |
| 2013/0113939 A1 | 5/2013 | Strandemar |
| 2014/0002639 A1 | 1/2014 | Cheben |
| 2014/0210984 A1 | 7/2014 | Warwick |
| 2015/0323449 A1 | 11/2015 | Jones |
| 2016/0084729 A1 | 3/2016 | Huseynov |
| 2017/0089800 A1 | 3/2017 | Huseynov |

OTHER PUBLICATIONS

Search Report dated Feb. 1, 2019 issued in European Patent Application No. 16859660.9.

Liebert, "A Master Engineering Report," Introduction to Clutter and Clutter Suppression Algorithms for Target Recognition in Infrared Imaging Systems, College of Engineering at Texas University, Oct. 25, 2008, 90 pages.

Office Action dated Oct. 4, 2019 issued in European Patent Application No. 16859660.9.

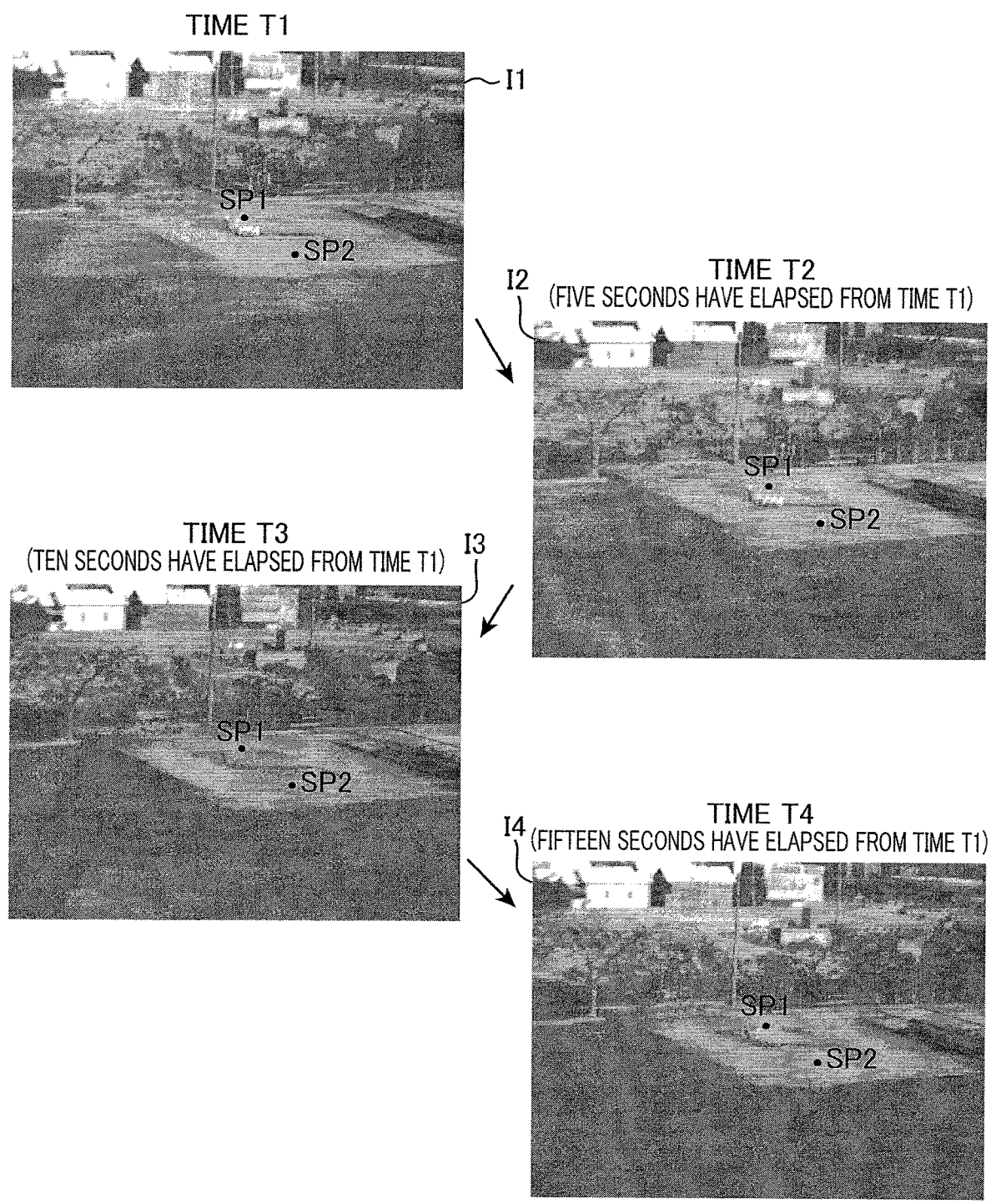

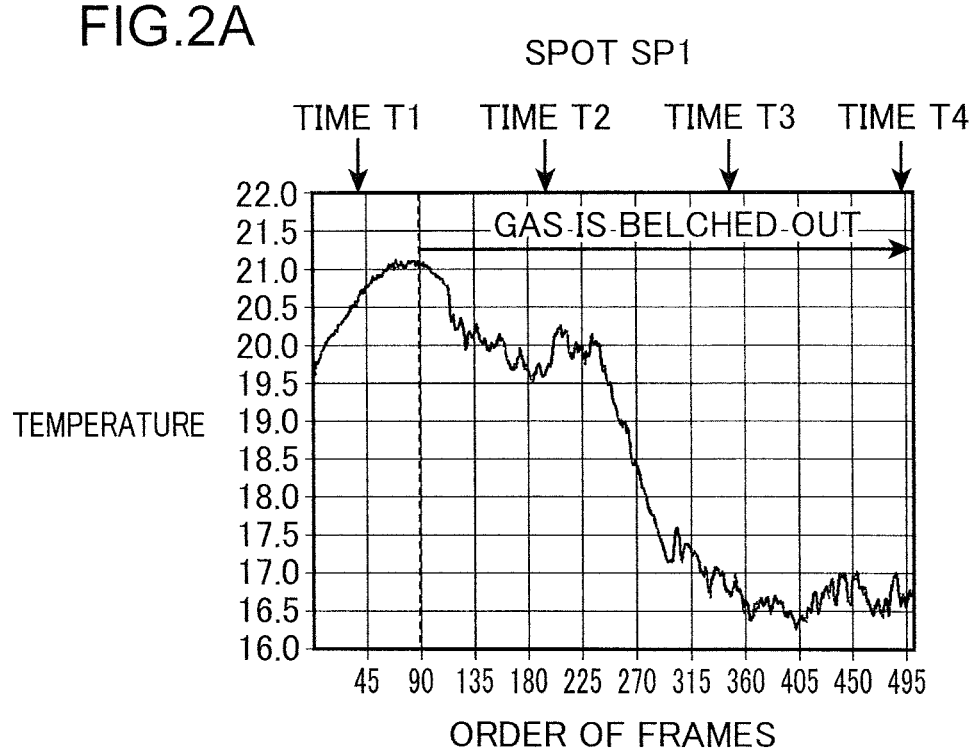

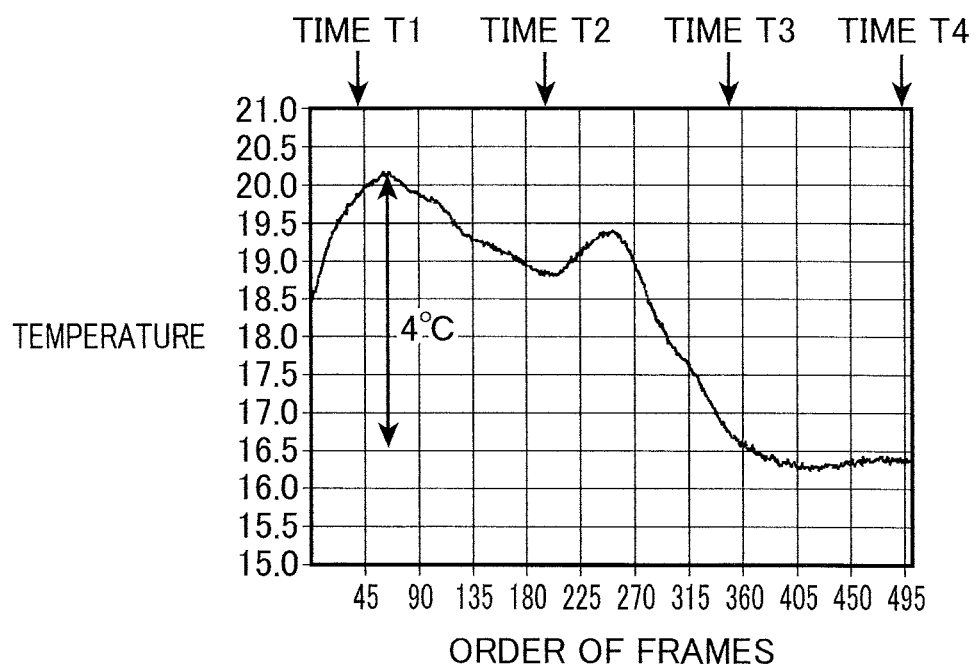

FIG.9
TIME T1
TIME T2
(FIVE SECONDS HAVE ELAPSED FROM TIME T1)
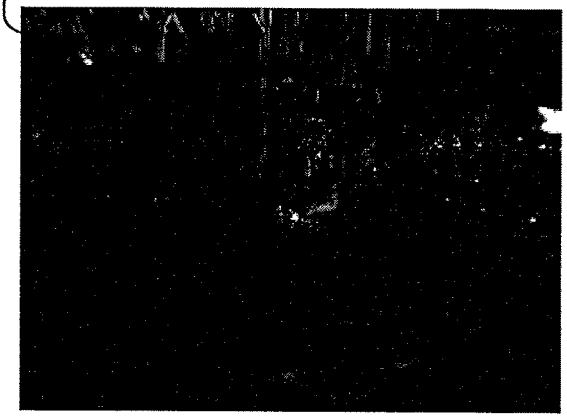
TIME T3
(TEN SECONDS HAVE ELAPSED FROM TIME T1)
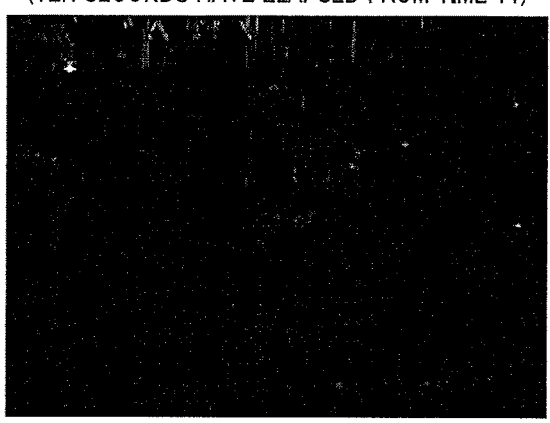
TIME T4
(FIFTEEN SECONDS HAVE ELAPSED FROM TIME T1)
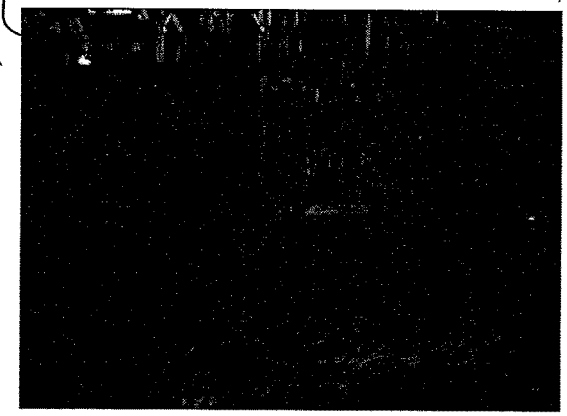

FIG.10
TIME T1
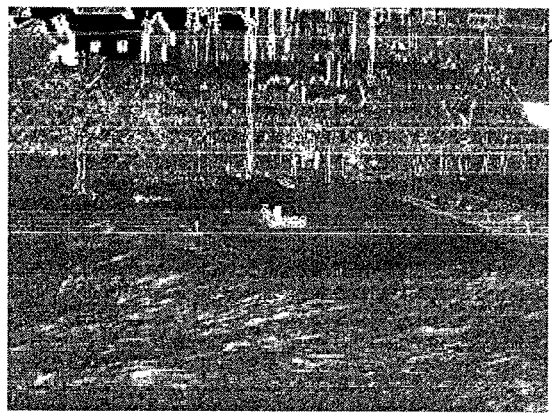
TIME T2
(FIVE SECONDS HAVE ELAPSED FROM TIME T1)
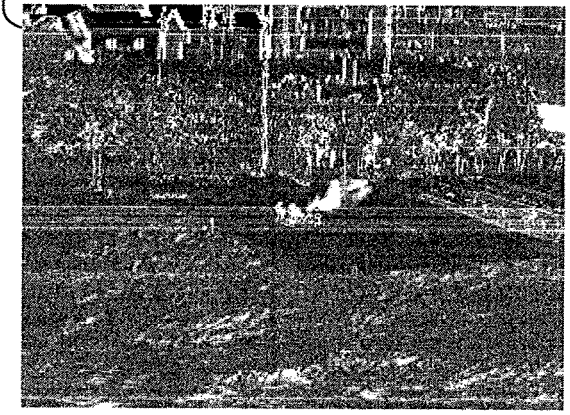
TIME T3
(TEN SECONDS HAVE ELAPSED FROM TIME T1)
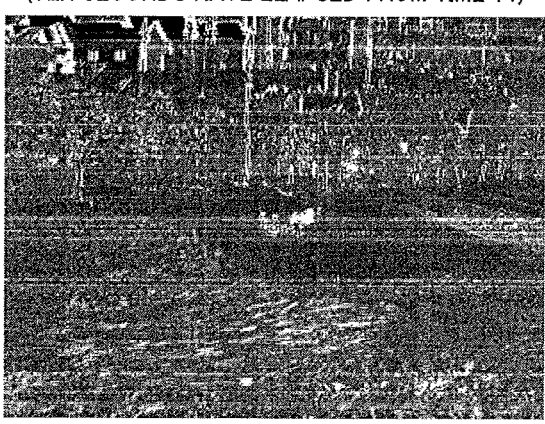
TIME T4
(FIFTEEN SECONDS HAVE ELAPSED FROM TIME T1)
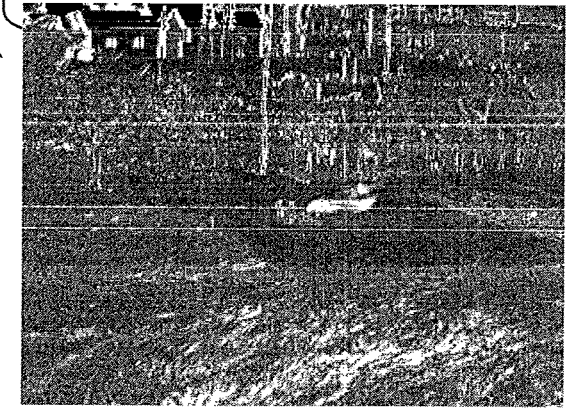

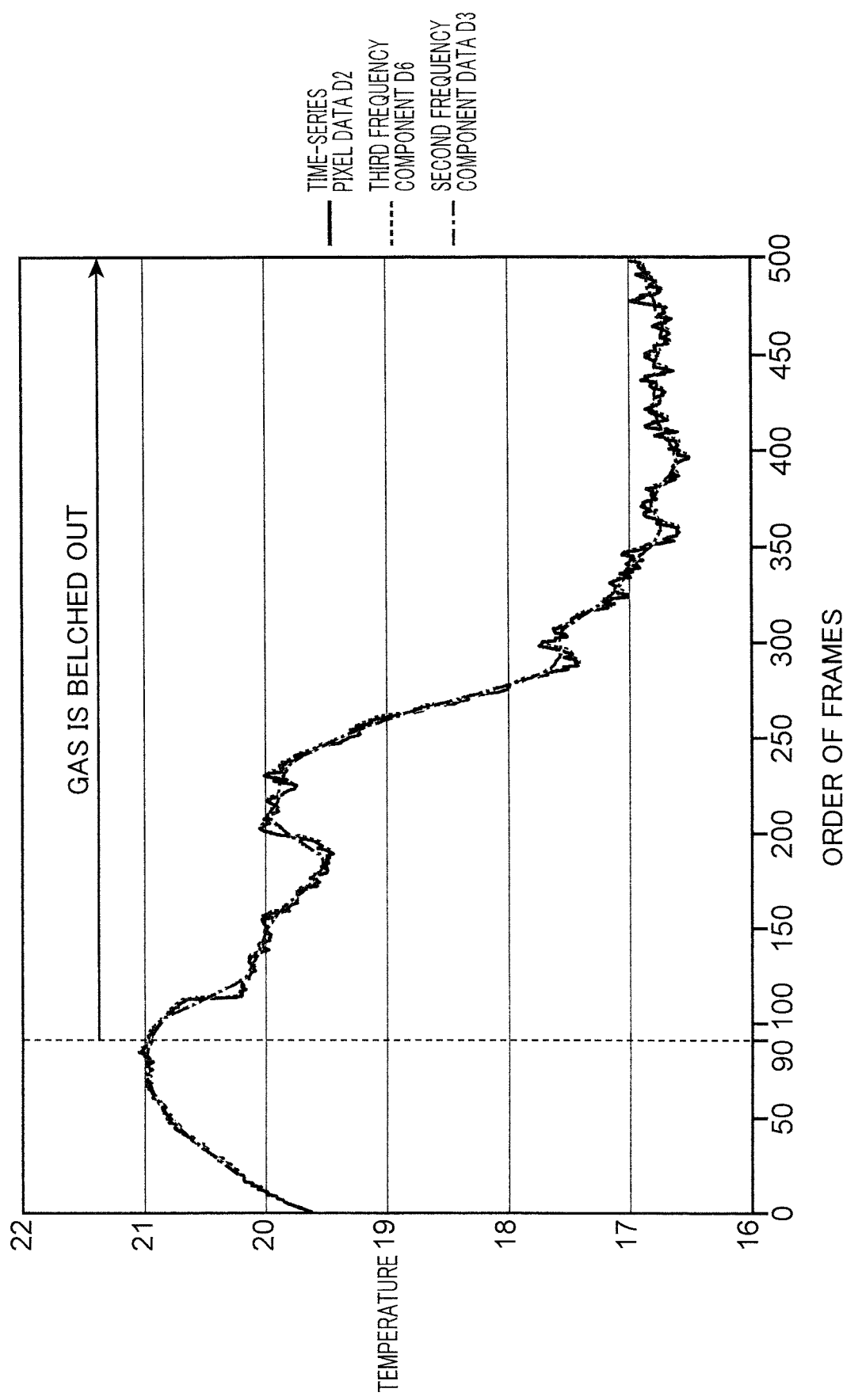

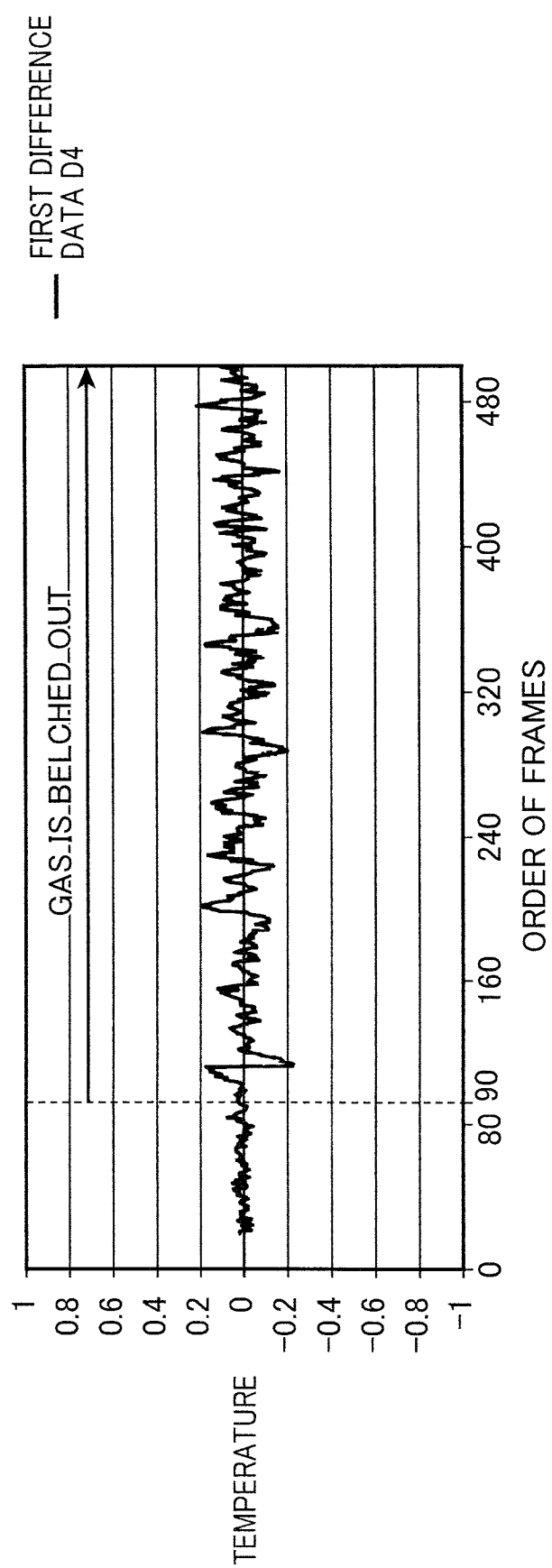

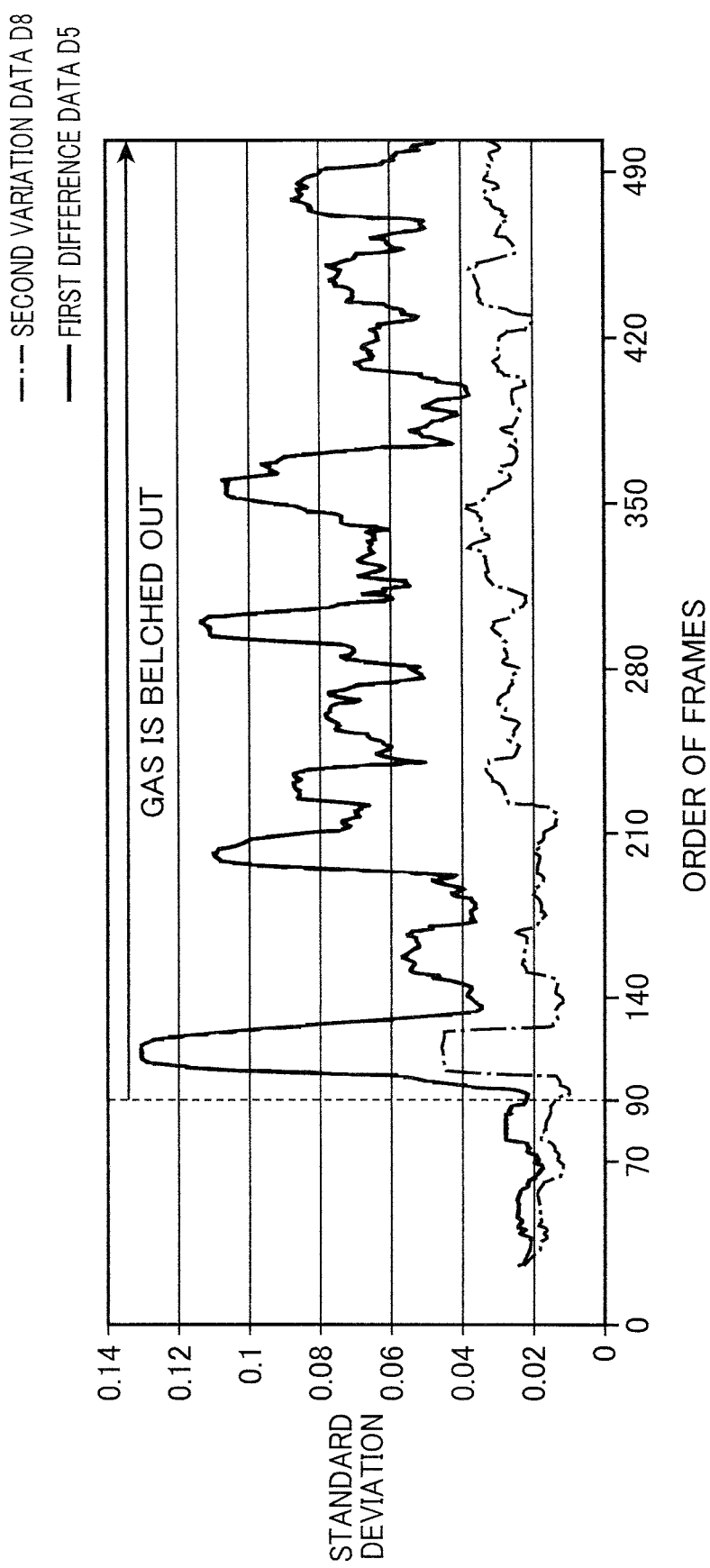

TIME T6

IMAGE PROCESSING DEVICE, IMAGE PROCESSING METHOD AND IMAGE PROCESSING PROGRAM

RELATED APPLICATIONS

This application is a continuation of U.S. patent application Ser. No. 15/770,273 filed Apr. 23, 2018, which is a U.S. National Stage of International Application No. PCT/JP2016/080968 filed Oct. 19, 2016, which claims priority of Japanese application no. 2015-212518 filed Oct. 29, 2015, the entire content of all of which are hereby incorporated by reference.

TECHNICAL FIELD

The present invention relates to a technique for image processing.

BACKGROUND ART

When a gas leak occurs, a slight temperature change occurs in a region where the leaking gas is drifting. As a technique for detecting a gas by using this principle, gas detection using infrared images is known. Since this enables real-time display of a moving image indicating how a gas is leaking (in other words, a region where the leaking gas is drifting), it is possible to intuitively determine a range of the gas leak.

As gas detection using infrared images, for example, Patent Literature 1 discloses a gas leak detection device including an infrared camera that shoots a region to be inspected and an image processing unit that processes infrared images shot by the infrared camera, and the image processing unit includes a fluctuation extraction unit that extracts dynamic fluctuation caused by a gas leak from a plurality of infrared images arranged on a time-series basis.

When a gas leak occurs, a temperature change caused by the leaking gas is small (e.g., 0.5° C.). For an outdoor object to be monitored for a gas leak (e.g., a place where gas transport pipes are connected to each other), when a cloud moves to block sunlight or a cloud blocking sunlight moves, the temperature of a background to be monitored changes more sharply and greatly than the temperature change caused by the leaking gas (e.g., 4° C.).

When the gas leak and the background temperature change occur in parallel, in a region where the leaking gas is drifting, the temperature change caused by the gas leak will coincide with the background temperature change. The inventors have found out that in such a case, if the background temperature change is larger than the temperature change caused by the leaking gas, unless the background temperature change is taken into consideration, it is not possible to display as infrared images how the gas is leaking, that is, it is difficult to detect the gas.

CITATION LIST

Patent Literature

Patent Literature 1: Japanese Patent Application Laid-Open No. 2012-58093

SUMMARY OF INVENTION

An image processing device according to a first aspect of the present invention is an image processing device for performing image processing obtained by shooting an object to be monitored at a plurality of time points, the image processing device including: a hardware processor that performs a process of removing, from image data indicating the images, second frequency component data lower in frequency than first frequency component data indicating a luminance change of the object to be monitored, the second frequency component data indicating a background luminance change of the object to be monitored.

BRIEF DESCRIPTION OF DRAWINGS

FIG. 1 is an image diagram illustrating, on a time-series basis, infrared images obtained by shooting an outdoor test site while a gas leak and a background temperature change occur in parallel.

FIG. 2A is a graph illustrating a temperature change at a spot SP1 in the test site.

FIG. 2B is a graph illustrating the temperature change at a spot SP2 in the test site.

FIG. 9 is an image diagram illustrating, on a time-series basis, one example of images processed by the first mode of the image processing unit.

FIG. 10 is an image diagram illustrating, on a time-series basis, another example of the images processed by the first mode of the image processing unit.

FIG. 12 is a graph illustrating the time-series pixel data D2 of the pixel corresponding to the spot SP1, the second frequency component data D3 extracted from the time-series pixel data D2, and third frequency component data D6 extracted from the time-series pixel data D2.

FIG. 13A is a graph illustrating the first difference data D4.

FIG. 14 is a graph illustrating the first variation data D5 and second variation data D8.

DESCRIPTION OF EMBODIMENT

Figure 3A:
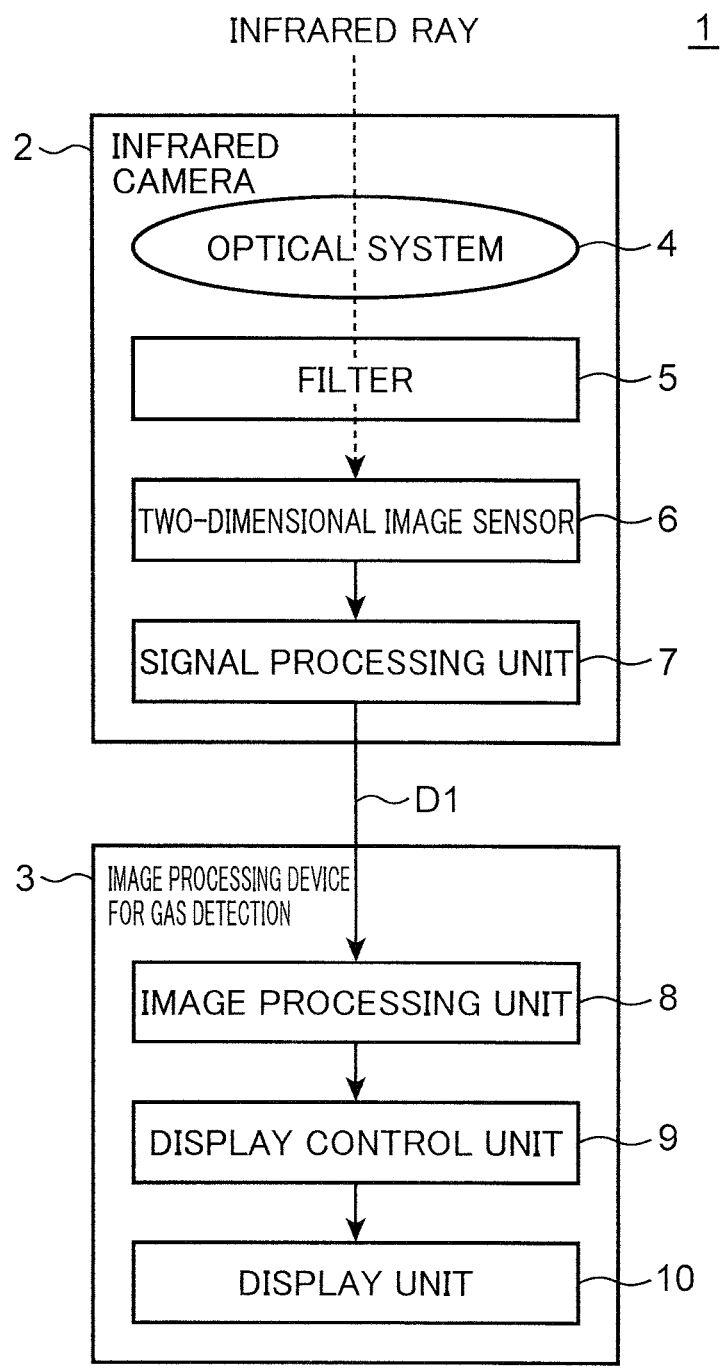
FIG. 3A is a block diagram illustrating a configuration of a gas detection device according to the present embodiment.

An embodiment of the present invention will be described in detail below with reference to the drawings. In each figure, a component denoted with the same reference symbol indicates the same component, and a description that has already been made for the component will be omitted.

The inventors have found out that, in gas detection using infrared images, when a gas leak and a background temperature change occur in parallel and the background temperature change is larger than the temperature change caused by the leaking gas, unless the background temperature change is taken into consideration, it is not possible to display as infrared images how the gas is leaking. This will be described in detail.

FIG. 1 is an image diagram illustrating, on a time-series basis, infrared images obtained by shooting an outdoor test site while a gas leak and a background temperature change occur in parallel. These are infrared images obtained by shooting a moving image with an infrared camera. At the test site, there is a spot SP1 where a gas can be belched out. For comparison with the spot SP1, a spot SP2 where a gas is not belched out is illustrated.

The infrared image I1 is an infrared image of the test site shot at a time T1 immediately before sunlight is blocked by a cloud. The infrared image I2 is an infrared image of the test site shot at a time T2 that is five seconds after the time T1. Since sunlight is blocked by a cloud at the time T2, the background temperature is lower than at the time T1.

The image I3 is an infrared image of the test site shot at a time T3 that is 10 seconds after the time T1. Since sunlight is continuously blocked by a cloud from the time T2 to the time T3, the background temperature is lower at the time T3 than at the time T2.

The image I4 is an infrared image of the test site shot at a time T4 that is 15 seconds after the time T1. Since sunlight is continuously blocked by a cloud from the time T3 to the time T4, the background temperature is lower at the time T4 than at the time T3.

In 15 seconds from the time T1 to the time T4, the background temperature decreases by about 4° C. For this reason, it is understood that the image I4 is darker than the image I1 as a whole, and that the background temperature has decreased.

At a time after the time T1 and before the time T2, a belch of a gas is started at the spot SP1. The temperature change caused by the belched gas is small (about 0.5° C.). Therefore, although the gas is belched out at the spot SP1 at the time T2, the time T3, and the time T4, the background temperature change is much larger than the temperature change caused by the belched gas, and thus it is unknown from the image I2, the image I3, and the image I4 how the gas is coming out from the spot SP1.

FIG. 2A is a graph illustrating the temperature change at the spot SP1 in the test site, and FIG. 2B is a graph illustrating the temperature change at the spot SP2 in the test site. Vertical axes of these graphs represent the temperature. Horizontal axes of these graphs represent order of frames. For example, a numeral 45 means the 45th frame. A frame rate is 30 fps. Therefore, the time from the first frame to the 450th frame is 15 seconds.

The graph indicating the temperature change at the spot SP1 is different from the graph indicating the temperature change at the spot SP2. Since a gas is not belched out at the spot SP2, the temperature change at the spot SP2 indicates the background temperature change. In contrast, since a gas is belched out at the spot SP1, the gas is drifting at the spot SP1. Therefore, the temperature change at the spot SP1 indicates the temperature change obtained by adding the background temperature change to the temperature change caused by the leaking gas.

It is understood from the graph illustrated in FIG. 2A that the gas is belched out at the spot SP1 (that is, it is understood that the gas leak has occurred at the spot SP1). However, as described above, it is unknown from the infrared images illustrated in FIG. 1 that the gas is belched out at the spot SP1 (that is, it is unknown that the gas leak has occurred at the spot SP1). The present embodiment makes it possible to indicate as images how a gas is leaking, by performing image processing on the infrared images by taking the background temperature change into consideration.

FIG. 3A is a block diagram illustrating a configuration of a gas detection system 1 according to the present embodiment. The gas detection system 1 includes an infrared camera 2 and an image processing device for gas detection 3.

The infrared camera 2 shoots a moving image of infrared images of an object to be monitored for a gas leak (e.g., a portion where gas transport pipes are connected to each other) and the background, and then generates moving image data D1 indicating the moving image. The moving image data D1 is one example of image data of the infrared images. The infrared images of the object to be monitored for a gas leak and the background may be shot not only as the moving image but also by the infrared camera 2 at a plurality of time points. The infrared camera 2 includes an optical system 4, a filter 5, a two-dimensional image sensor 6, and a signal processing unit 7.

The optical system 4 forms infrared images of a subject (object to be monitored and background) on the two-dimensional image sensor 6. The filter 5 is disposed between the optical system 4 and the two-dimensional image sensor 6, and transmits only an infrared ray having a specific wavelength among light having passed through the optical system 4. Among infrared wavelength bands, a wavelength band that is allowed to pass through the filter 5 depends on a type of gas to be detected. For example, for methane, the filter 5 that transmits the wavelength band of 3.2 to 3.4 µm is used. The two-dimensional image sensor 6 is, for example, a cooled indium antimony (InSb) image sensor, and receives an infrared ray that has passed through the filter 5. The signal processing unit 7 converts an analog signal output from the two-dimensional image sensor 6 into a digital signal and then performs known image processing. This digital signal becomes the moving image data D1.

Figure 4:
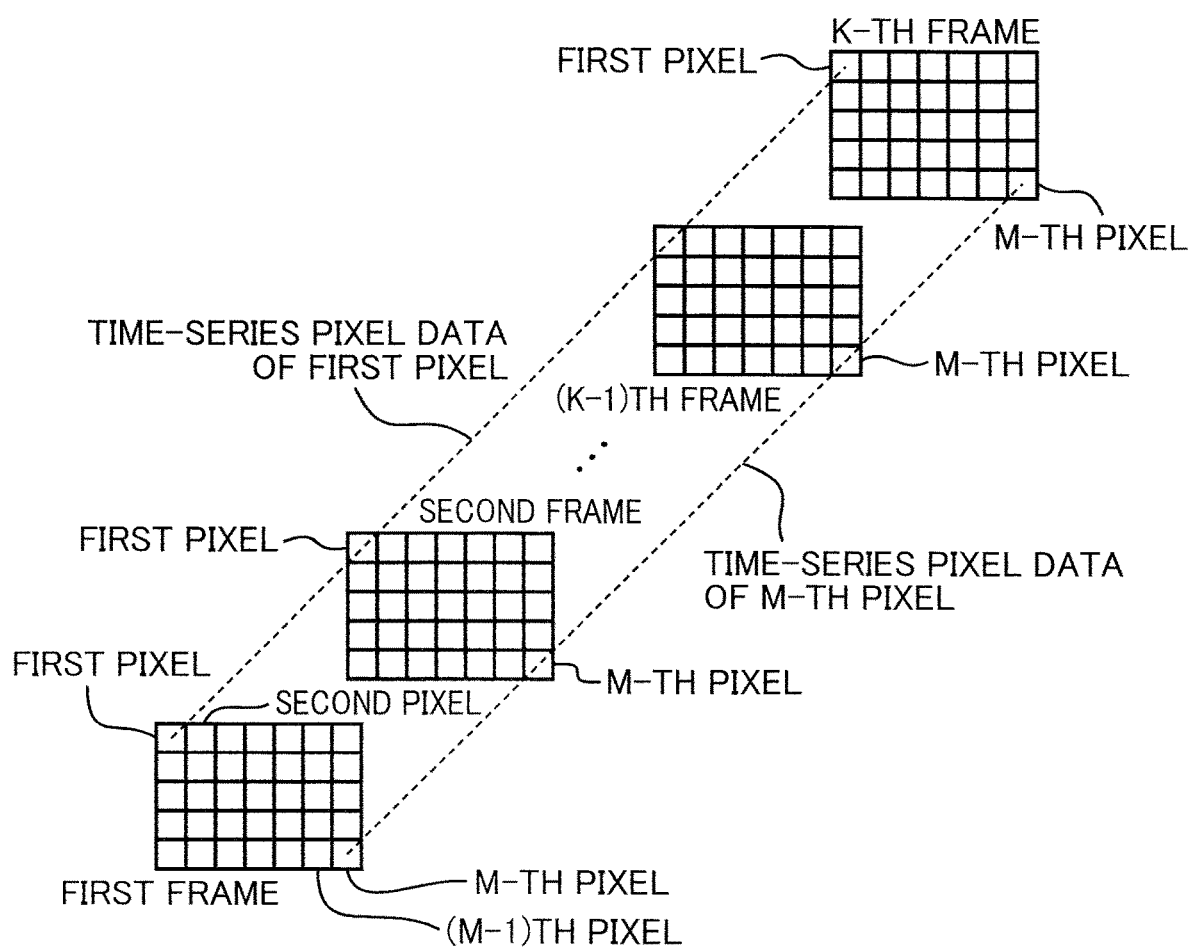
FIG. 4 is an explanatory diagram explaining time-series pixel data.

The moving image indicated by the moving image data D1 (image data) has a structure in which a plurality of frames is arranged on a time-series basis. It is assumed that data obtained by arranging pixel data of pixels at identical positions of the plurality of frames on a time-series basis is time-series pixel data. The time-series pixel data will be specifically described. FIG. 4 is an explanatory diagram explaining the time-series pixel data. It is assumed that the number of frames of the moving image of the infrared images is K. It is assumed that one frame includes M pixels, that is, a first pixel, a second pixel, . . . , an (M−1)th pixel, and an M-th pixel. The pixel data indicates luminance or temperature of the pixel.

The pixels at the identical position in the plurality of (K) frames mean pixels in the same order. For example, when description is made for the first pixel, data obtained by arranging the following pixel data on a time-series basis is the time-series pixel data of the first pixel: pixel data of the first pixel included in the first frame, pixel data of the first pixel included in the second frame, . . . , pixel data of the first pixel included in the (K−1)th frame, and pixel data of the first pixel included in the K-th frame. Also, when description is made for the M-th pixel, data obtained by arranging the following pixel data on a time-series basis is the time-series pixel data of the M-th pixel: pixel data of the M-th pixel included in the first frame, pixel data of the M-th pixel included in the second frame, . . . , pixel data of the M-th pixel included in the (K−1)th frame, and pixel data of the M-th pixel included in the K-th frame. The number of time-series pixel data is the same as the number of pixels constituting one frame, and the plurality of (M) time-series pixel data constitutes the moving image data D1.

Returning to the description of FIG. 3A, the image processing device for gas detection 3 is a device such as a personal computer, a smartphone, and a tablet terminal, and includes, as functional blocks, an image processing unit 8, a display control unit 9, and a display unit 10. The image processing unit 8 and the display control unit 9 are implemented by devices such as a central processing unit (CPU), a random access memory (RAM), a read only memory (ROM), and a hard disk drive (HDD). The display unit 10 is implemented by, for example, a liquid crystal display.

The image processing unit 8 performs a predetermined process on the moving image data D1 (image data). The predetermined process includes a process of removing second frequency component data from the moving image data D1. This process will be described. When a gas leak occurs while the infrared camera 2 is shooting a moving image of the object to be monitored for a gas leak and the background, the moving image data D1 includes first frequency component data indicating the temperature change caused by the leaking gas. Of the moving image of the infrared images, an image indicated by the first frequency component data indicates how the gas is leaking (in other words, a region where the leaking gas is drifting).

The inventors have found out the following phenomenon. While the infrared camera 2 is shooting the moving image of the object to be monitored for a gas leak and the background, when the gas leak and the background temperature change occur in parallel and the background temperature change is larger than the temperature change caused by the leaking gas, it is unknown from the moving image of the infrared images how the gas is leaking. This is because, in addition to the first frequency component data, the moving image data D1 includes the second frequency component data that is lower in frequency than the first frequency component data and indicates the background temperature change. The image indicated by the first frequency component data becomes invisible due to an image indicated by the second frequency component data (this image is a change in contrast between light and shade of the background). With reference to FIG. 2A, a small change included in the graph indicating the temperature change at the spot SP1 corresponds to the first frequency component data. The graph indicating the temperature change at the spot SP2 corresponds to the second frequency component data.

Therefore, the image processing unit 8 performs the process of removing the second frequency component data from each of the plurality of time-series pixel data having different pixel positions (that is, the plurality of time-series pixel data constituting the moving image data D1). The plurality of time-series pixel data having different pixel positions means, with reference to FIG. 4, the time-series pixel data of the first pixel, the time-series pixel data of the second pixel, . . . , the time-series pixel data of the (M−1)th pixel, and the time-series pixel data of the M-th pixel. The image processing unit 8 does not perform the process of removing the second frequency component data in units of frames, but performs the process of removing the second frequency component data in units of time-series pixel data. The process to be performed by the image processing unit 8 will be described in more detail later.

The display control unit 9 causes the display unit 10 to display the moving image indicated by the moving image data D1 that has undergone the predetermined process performed by the image processing unit 8.

Figure 3B:
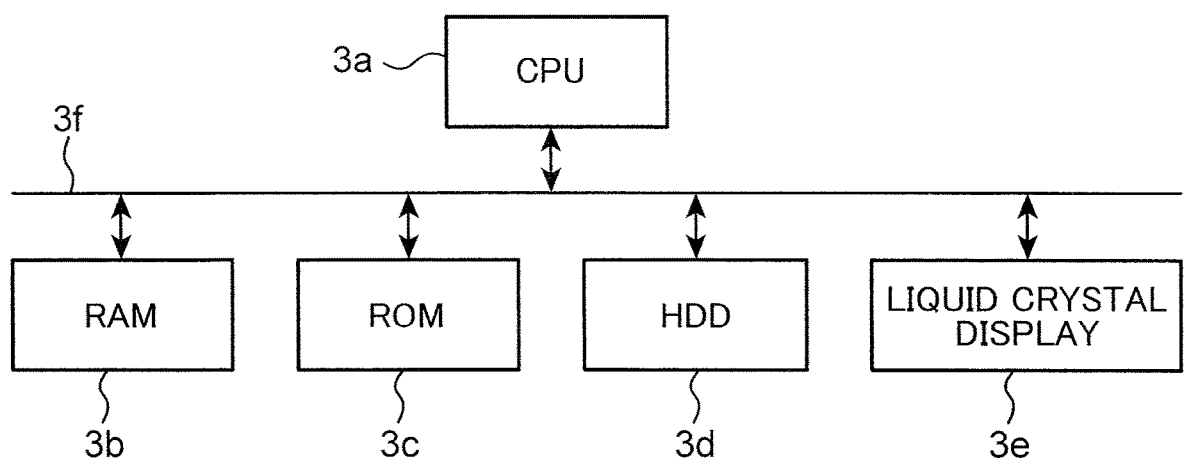
FIG. 3B is a block diagram illustrating a hardware configuration of an image processing device for gas detection illustrated in FIG. 3A.

FIG. 3B is a block diagram illustrating a hardware configuration of the image processing device for gas detection 3 illustrated in FIG. 3A. The image processing device for gas detection 3 includes a CPU 3a, a RAM 3b, a ROM 3c, an HDD 3d, a liquid crystal display 3e, and a bus 3f connecting these components. The liquid crystal display 3e is hardware that implements the display unit 10. Instead of the liquid crystal display 3e, an organic light emitting diode (EL) display, a plasma display, or the like may be used.

Programs for implementing functional blocks of the image processing unit 8 and the display control unit 9 illustrated in FIG. 3A have been stored in the HDD 3d (this may be a ROM 3c instead of the HDD 3d). The program that implements the image processing unit 8 is a processing program that acquires the moving image data D1 (image data) and performs the predetermined process on the moving image data D1. The program that implements the display control unit 9 is a display control program that causes the display unit 10 to display images (e.g., a moving image indicated by the moving image data D1 that has undergone the predetermined process). These programs may be stored in the ROM 3c instead of in the HDD 3d.

The CPU 3a implements these functional blocks by reading the processing program and the display control program from the HDD 3d, developing the programs in the RAM 3b, and executing the developed programs. The processing program and the display control program may be stored in advance in the HDD 3d, or a storage medium (for example, an external storage medium such as a magnetic disk or an optical disk) may be prepared in which these programs have been stored, and the programs stored in this storage medium may be stored in the HDD 3d.

Note that, as will be described next, the image processing unit 8 has first to seventh modes. Each of these modes includes a plurality of elements. Therefore, programs for implementing these elements have been stored in the HDD 3d. For example, the first mode of the image processing unit 8 includes, as elements, a first extraction unit, a first calculation unit, and a second calculation unit. Programs for implementing the first extraction unit, the first calculation unit, and the second calculation unit have been stored in the HDD 3d. These programs are expressed as a first extraction program, a first calculation program, and a second calculation program.

These programs are expressed using definitions of the elements. The first extraction unit and the first extraction program will be described as an example. The first extraction unit defines, as the second frequency component data, data extracted from the time-series pixel data by calculating a simple moving average of the time-series pixel data in units of the first predetermined number of frames smaller than the K frames illustrated in FIG. 4. The first extraction unit extracts the M second frequency component data corresponding to each of the M time-series pixel data illustrated in FIG. 4. The first extraction program is a program that defines, as the second frequency component data, data extracted from the time-series pixel data by calculating a simple moving average of the time-series pixel data in units of the first predetermined number of frames smaller than the K frames illustrated in FIG. 4. The first extraction program extracts the M second frequency component data corresponding to each of the M time-series pixel data illustrated in FIG. 4.

Figure 5:
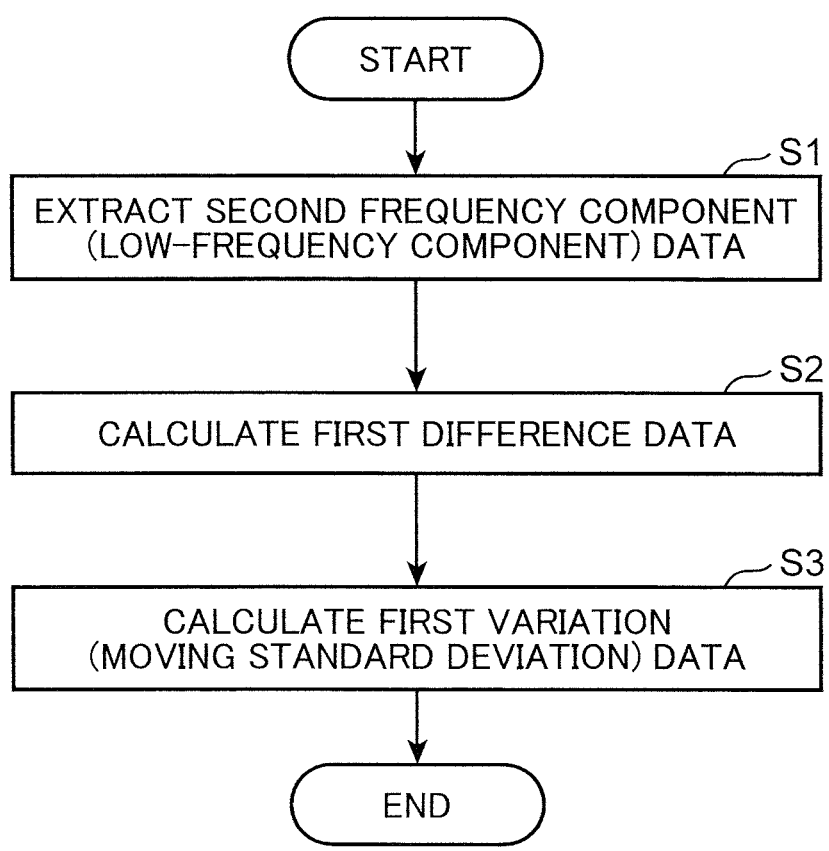
FIG. 5 is a flowchart of a process to be executed by a first mode of an image processing unit.

A flowchart of these programs to be executed by the CPU 3a (the first extraction program, the first calculation program, and the second calculation program) is FIG. 5 to be described later.

The first mode of the image processing unit 8 will be described. FIG. 5 is a flowchart of the process to be executed by the first mode of the image processing unit 8. The first mode of the image processing unit 8 functions as the first extraction unit. The first extraction unit defines, as the second frequency component data, data extracted from the time-series pixel data by calculating a simple moving average of the time-series pixel data in units of the first predetermined number of frames smaller than the K frames illustrated in FIG. 4. The first extraction unit extracts the M second frequency component data corresponding to each of the M time-series pixel data illustrated in FIG. 4 (step S1).

Figure 6:
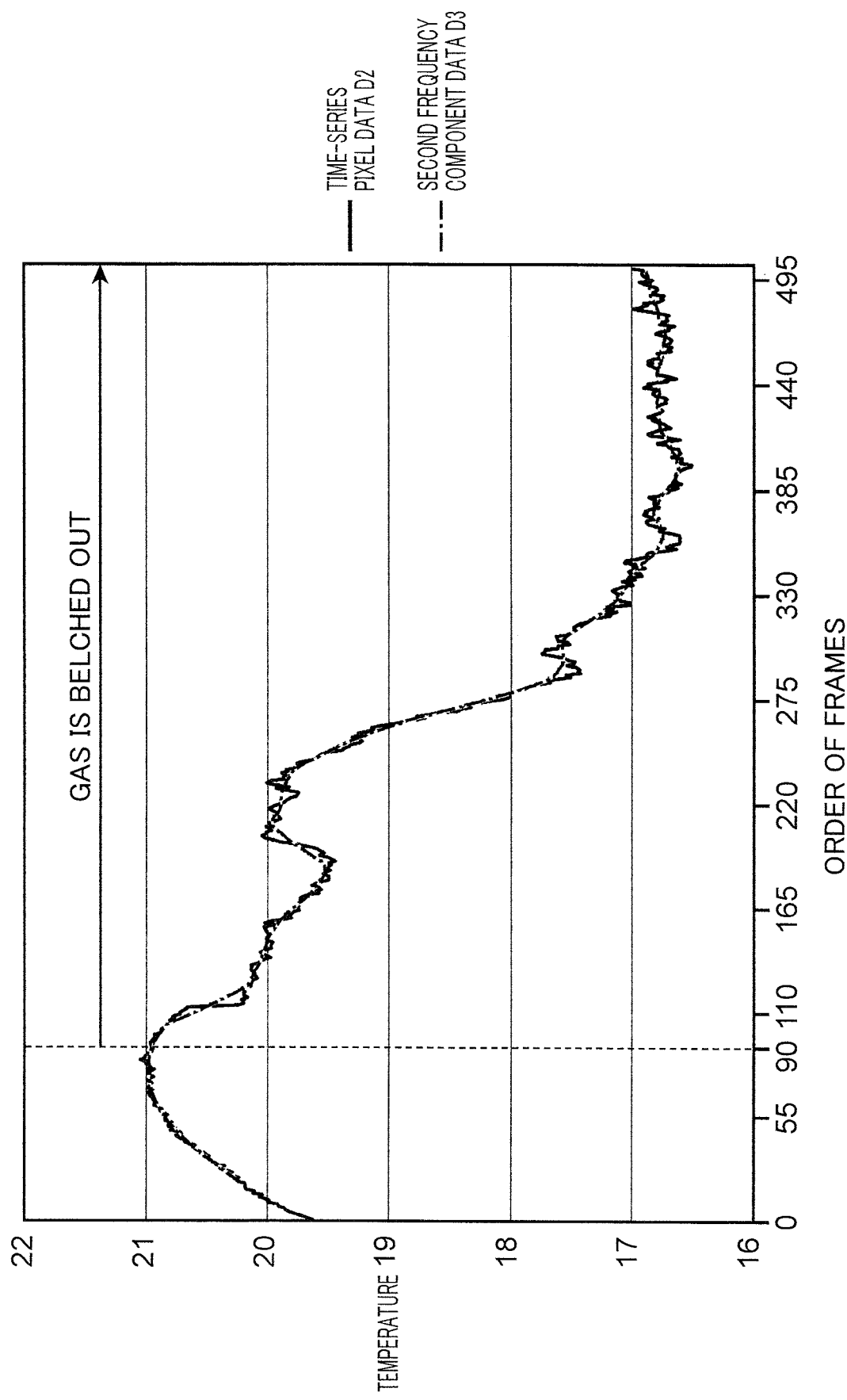
FIG. 6 is a graph illustrating time-series pixel data D2 of pixels corresponding to the spot SP1 and second frequency component data D3 extracted from this time-series pixel data D2.

FIG. 6 is a graph illustrating the time-series pixel data D2 of the pixels corresponding to the spot SP1 in FIG. 2A and the second frequency component data D3 extracted from this time-series pixel data D2. The temperature indicated by the time-series pixel data D2 changes relatively rapidly (change period is relatively short), whereas the temperature indicated by the second frequency component data D3 changes relatively slowly (change period is relatively long). A vertical axis and a horizontal axis of the graph are the same as the vertical axis and the horizontal axis of the graph of FIG. 2A, respectively. That is, the vertical axis of the graph represents the temperature. The horizontal axis of the graph represents the order of frames.

The first predetermined number of frames is, for example, 21 frames. The breakdown is a target frame, ten consecutive frames before the target frame, and ten consecutive frames after the target frame. The first predetermined number is required at least to be the number that allows extraction of the second frequency component data from the time-series pixel data, and the first predetermined number is not limited to 21, but may be more than 21 or less than 21.

The first mode of the image processing unit 8 functions as the first calculation unit. The first calculation unit defines, as first difference data, data obtained by calculating a difference between the time-series pixel data and the second frequency component data extracted from this time-series pixel data, and calculates the M first difference data corresponding to each of the M time-series pixel data (step S2).

Figure 7:
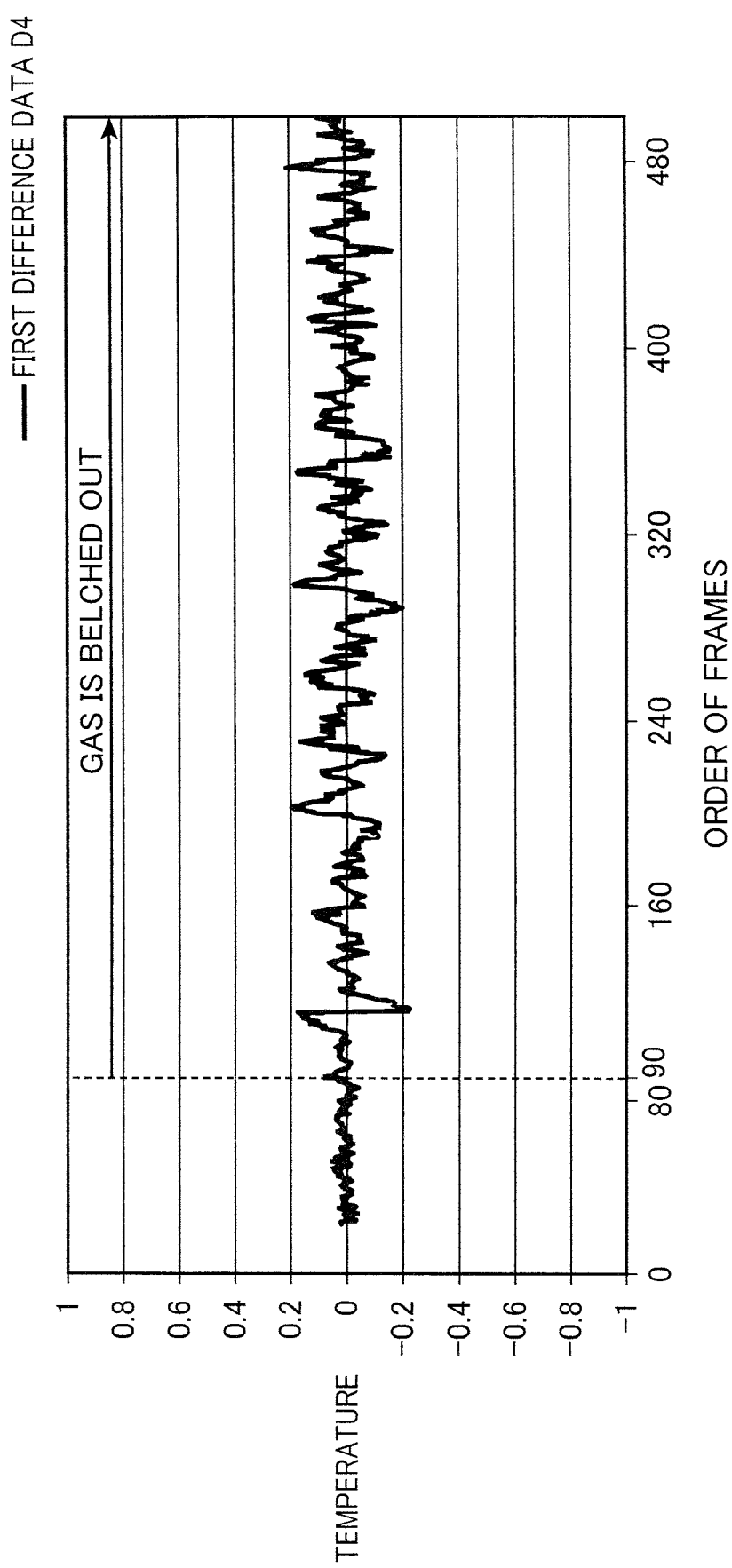
FIG. 7 is a graph illustrating first difference data D4.

FIG. 7 is a graph illustrating the first difference data D4. A vertical axis and a horizontal axis of the graph are the same as the vertical axis and the horizontal axis of the graph of FIG. 2A, respectively. The first difference data D4 is data obtained by calculating the difference between the time-series pixel data D2 and the second frequency component data D3 illustrated in FIG. 6. Before the belch of a gas starts at the spot SP1 (frames before about 90th frame), repetition of minute amplitude indicated by the first difference data D4 mainly indicates sensor noise of the two-dimensional image sensor 6. After the belch of a gas starts at the spot SP1 (frames after 90th frame), variations in the amplitude and the waveform of the first difference data D4 have become larger.

The image processing unit 8 functions as the second calculation unit. The second calculation unit defines, as first fluctuation data, data indicating a fluctuation in the first difference data calculated by performing a predetermined operation on the first difference data in units of the second predetermined number of frames. The second calculation unit calculates the plurality of (M) first fluctuation data corresponding to each of the plurality of (M) time-series pixel data illustrated in FIG. 4. There are two types of first fluctuation data: one is first variation data and the other is first absolute value addition data. The first mode of the image processing unit 8 uses the first variation data as the first fluctuation data. The first variation data is data indicating the variation in the waveform of the first difference data.

In the first mode of the image processing unit 8, the second calculation unit defines, as the first variation data, data obtained by calculating a moving standard deviation of the first difference data in units of the second predetermined number of frames smaller than the K frames. The second calculation unit calculates the M first variation data corresponding to each of the M time-series pixel data (step S3). Note that instead of the moving standard deviation, moving dispersion may be calculated.

Figure 8:
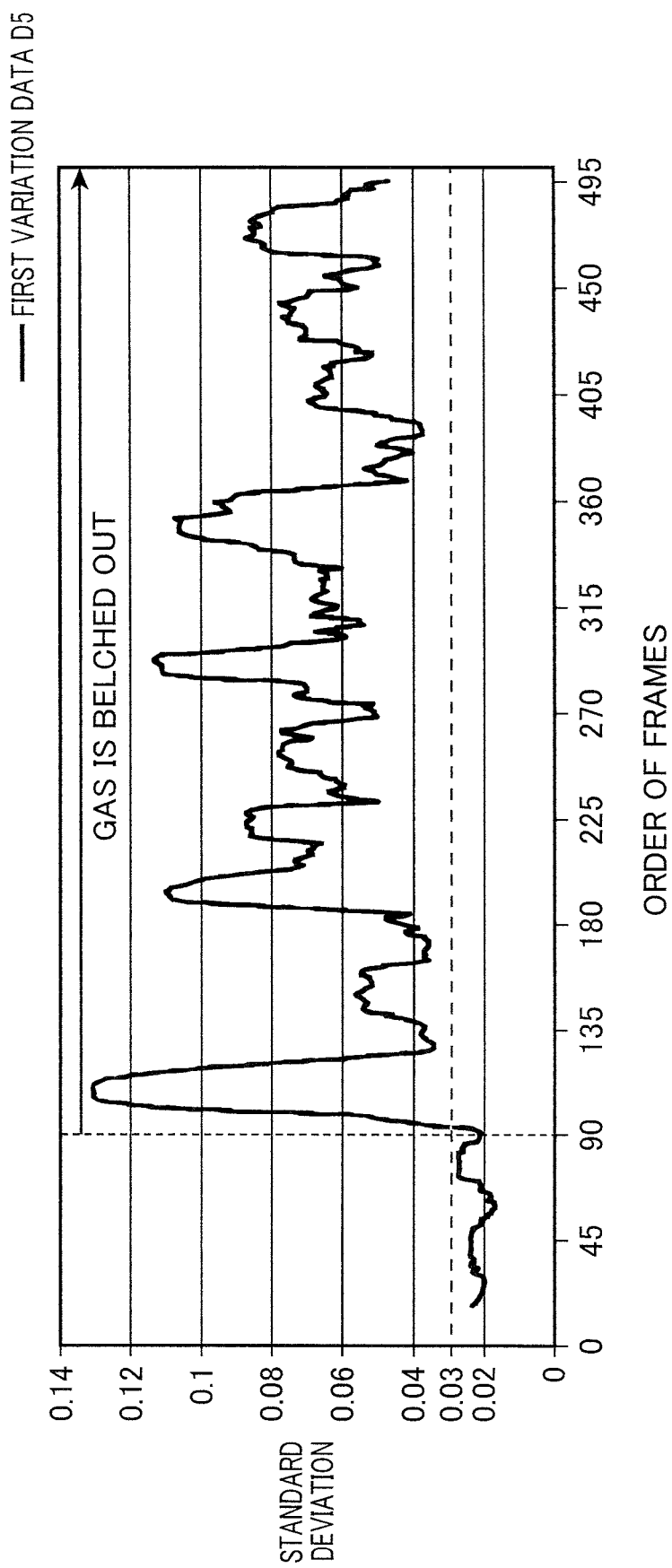
FIG. 8 is a graph illustrating first variation data D5.

FIG. 8 is a graph illustrating the first variation data D5. A horizontal axis of the graph is the same as the horizontal axis of the graph of FIG. 2A. A vertical axis of the graph represents a standard deviation. The first variation data D5 is data indicating the moving standard deviation of the first difference data D4 illustrated in FIG. 7. The second predetermined number of frames is, for example, 21 frames. Since the second predetermined number is required at least to be the number that allows calculation of a statistically significant standard deviation, the second predetermined number may be the same as or different from the first predetermined number.

As illustrated in FIG. 8, by setting a threshold of the standard deviation indicating a gas leak (e.g., 0.03), the first mode of the image processing unit 8 can detect the gas leak. When the first mode of the image processing unit 8 detects the gas leak, the display control unit 9 illustrated in FIG. 3A may cause the display unit 10 to display that the gas leak is detected, and the image processing device for gas detection 3 may operate an unillustrated alarm (speaker) to notify that the gas leak is detected. This display and notification of the gas leak detection are also applicable to the second to seventh modes of the image processing unit 8 to be described later.

The display control unit 9 defines the M first variation data obtained in step S3 as the moving image data D1 that has undergone the process of removing the second frequency component data, and causes the display unit 10 to display the moving image indicated by the moving image data D1. In this moving image, images of frames at the time T1, the time T2, the time T3, and the time T4 are illustrated in FIGS. 9 and 10. FIGS. 9 and 10 are image diagrams illustrating, on a time-series basis, one example of the images processed by the first mode of the image processing unit 8. In generation of these images, a coefficient that determines a magnification of the moving standard deviation is different, whereby these images differ in contrast.

FIG. 9 illustrates an image I5, an image I6, an image I7, and an image I8 obtained in step S3 with the standard deviation of 1000, whereas FIG. 10 illustrates an image I9, an image I10, an image I11, and an image I12 obtained in step S3 with the standard deviation of 5000. The images I5 and I9 are images obtained by processing the infrared image I1 illustrated in FIG. 1 by the first mode of the image processing unit 8. The images I6 and I10 are images obtained by processing the infrared image I2 illustrated in FIG. 1 by the first mode of the image processing unit 8. The images I7 and I11 are images obtained by processing the infrared image I3 illustrated in FIG. 1 by the first mode of the image processing unit 8. The images I8 and I12 are images obtained by processing the infrared image I4 illustrated in FIG. 1 by the first mode of the image processing unit 8. In both FIGS. 9 and 10, it is understood that the gas is belched out at the spot SP1.

As described above, with the first mode of the image processing unit 8, the image processing unit 8 performs the process of removing the second frequency component data included in the moving image data D1, and then the display control unit 9 causes the display unit 10 to display the moving image indicated by the moving image data D1 that has undergone this process. Therefore, even when the gas leak and the background temperature change occur in parallel and the background temperature change is larger than the temperature change caused by the leaking gas, the first mode of the image processing unit 8 can display as the moving image how the gas is leaking.

Figure 11:
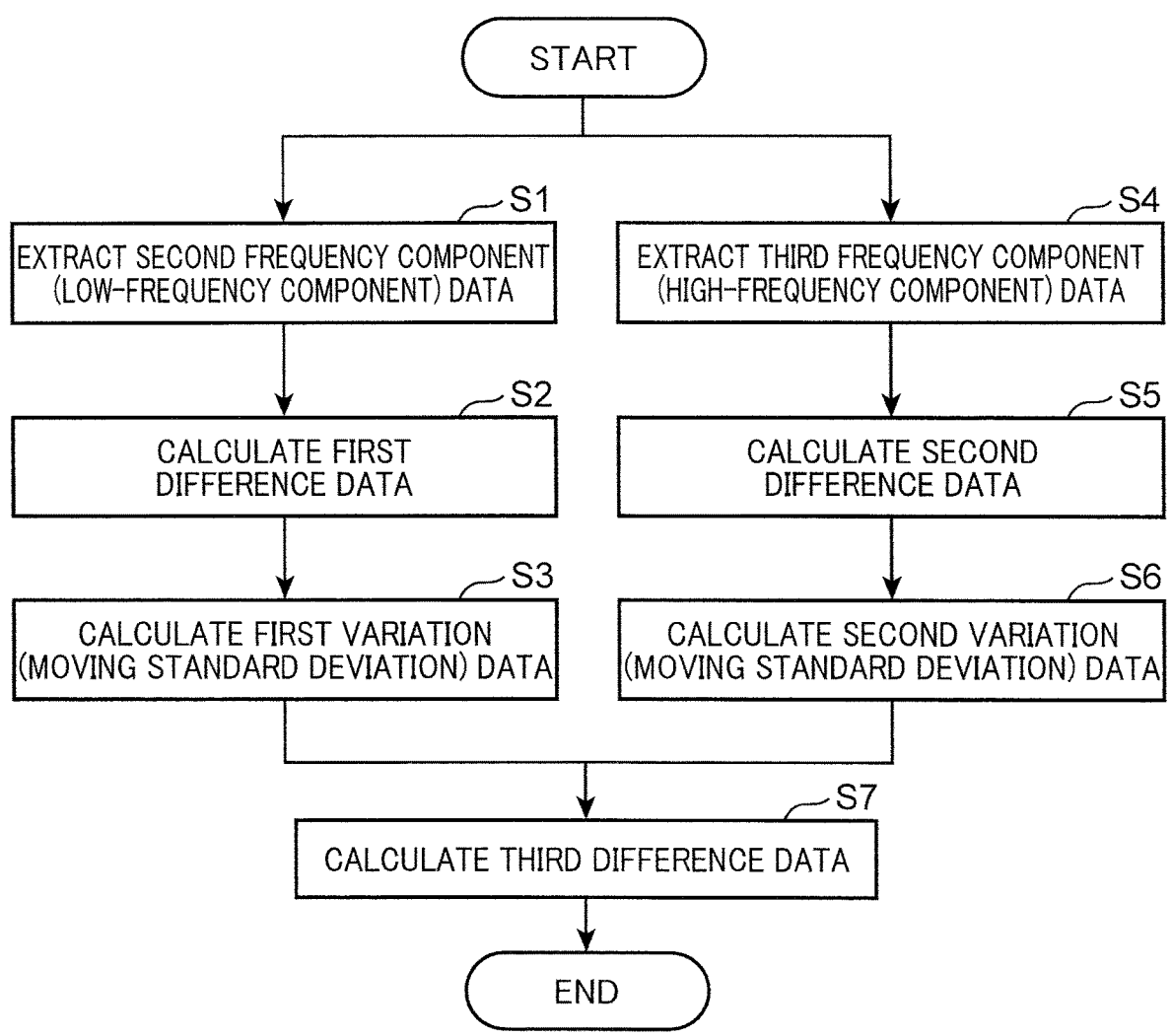
FIG. 11 is a flowchart of a process to be executed by a second mode of the image processing unit.

The second mode of the image processing unit 8 will be described. The second mode of the image processing unit 8 perform the process of removing, in addition to the second frequency component data indicating the background temperature change, third frequency component data indicating high-frequency noise from the moving image data D1. The high-frequency noise is mainly sensor noise of the two-dimensional image sensor 6. The third frequency component data is higher in frequency than the first frequency component data indicating the temperature change caused by the leaking gas. The second mode of the image processing unit 8 transmits the first frequency component data indicating the temperature change caused by the leaking gas, and cuts the second frequency component data that is lower in frequency than the first frequency component data, and the third frequency component data that is higher in frequency than the first frequency component data. Therefore, the second mode of the image processing unit 8 functions as a band pass filter. FIG. 11 is a flowchart of the process to be executed by the second mode of the image processing unit 8.

The second mode of the image processing unit 8 functions as the first extraction unit that executes step S1, that is, extracts the second frequency component data. This function has been described in the first mode of the image processing unit 8. The second mode of the image processing unit 8 functions as a second extraction unit. The second extraction unit defines, as the third frequency component data, data extracted from the time-series pixel data by calculating a simple moving average of the time-series pixel data in units of the third predetermined number (e.g., 3) of frames that is smaller than the first predetermined number (e.g., 21). The second extraction unit extracts the M third frequency component data corresponding to each of the M time-series pixel data illustrated in FIG. 4 (step S4).

FIG. 12 is a graph illustrating the time-series pixel data D2 of the pixels corresponding to the spot SP1, the second frequency component data D3 extracted from the time-series pixel data D2, and the third frequency component data D6 extracted from the time-series pixel data D2. A vertical axis and a horizontal axis of the graph are the same as the vertical axis and the horizontal axis of the graph of FIG. 2A, respectively. FIG. 12 is a graph obtained by adding the third frequency component data D6 to the graph illustrated in FIG. 6. The temperature indicated by the time-series pixel data D2 changes relatively rapidly (change period is relatively short), whereas the temperature indicated by the second frequency component data D3 changes relatively slowly (change period is relatively long). The third frequency component data D6 substantially overlaps the time-series pixel data D2.

The third predetermined number of frames is, for example, three frames. The breakdown is a target frame, one frame immediately before the target frame, and one frame immediately after the target frame. The third predetermined number is required at least to be the number that allows extraction of the third frequency component data from the time-series pixel data, and the third predetermined number is not limited to three, but may be more than three.

The second mode of the image processing unit 8 functions as the first calculation unit that executes step S2, that is, calculates the first difference data. This function has been described in the first mode of the image processing unit 8. The second mode of the image processing unit 8 functions as a third calculation unit. The third calculation unit defines, as second difference data, data obtained by calculating a difference between the time-series pixel data and the third frequency component data extracted from the time-series pixel data. The third calculation unit calculates the M second difference data corresponding to each of the M time-series pixel data (step S5).

Figure 13B:
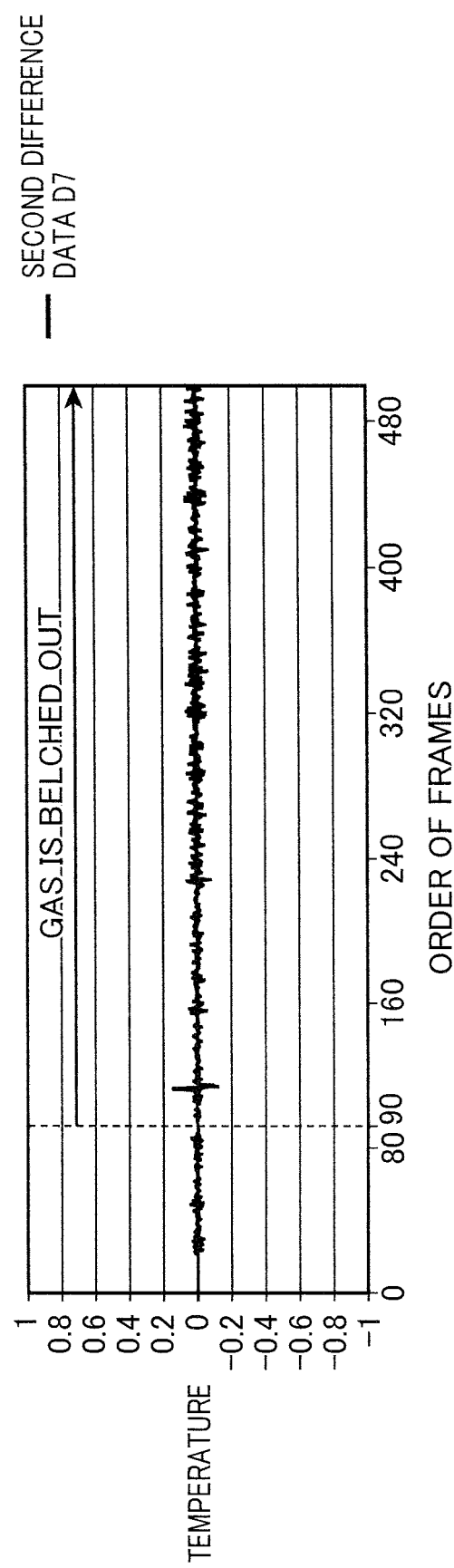
FIG. 13B is a graph illustrating second difference data D7.

FIG. 13A is a graph illustrating the first difference data D4, whereas FIG. 13B is a graph illustrating the second difference data D7. Vertical axes and horizontal axes of these graphs are the same as the vertical axis and the horizontal axis of the graph of FIG. 2A, respectively. The first difference data D4 is the same as the first difference data D4 illustrated in FIG. 7, and is data obtained by calculating a difference between the time-series pixel data D2 and the second frequency component data D3 illustrated in FIG. 12. The second difference data D7 is data obtained by calculating a difference between the time-series pixel data D2 and the third frequency component data D6 illustrated in FIG. 12.

The first difference data D4 includes the first frequency component data (data indicating the temperature change caused by the leaking gas) and the third frequency component data D6 (data indicating high-frequency noise). The second difference data D7 does not include the first frequency component data but includes the third frequency component data D6.

Since the first difference data D4 includes the first frequency component data, after the belch of a gas starts at the spot SP1 (90th and subsequent frames), amplitude and waveform variation of the first difference data D4 are large. In contrast, since the second difference data D7 does not include the first frequency component data, such a situation does not occur. The second difference data D7 repeats minute amplitude. This is the high-frequency noise.

The first difference data D4 and the second difference data D7 are correlated but not completely correlated. That is, in some frame, the first difference data D4 may have a positive value whereas the second difference data D7 may have a negative value, and vice versa. Therefore, even if a difference between the first difference data D4 and the second difference data D7 is calculated, the third frequency component data D6 cannot be removed. To remove the third high-frequency component data D6, it is necessary to convert the first difference data D4 and the second difference data D7 into absolute values.

Therefore, the second mode of the image processing unit 8 functions as the second calculation unit that executes step S3, that is, calculates the first variation data. This function has been described in the first mode of the image processing unit 8.

The image processing unit 8 functions as a fourth calculation unit. The fourth calculation unit defines, as the second fluctuation data, data indicating a fluctuation in the second difference data calculated by performing a predetermined operation on the second difference data in units of the fourth predetermined number of frames. The fourth calculation unit calculates the plurality of (M) second fluctuation data corresponding to each of the plurality of (M) time-series pixel data illustrated in FIG. 4. There are two types of second fluctuation data: one is second variation data and the other is second absolute value addition data. The second mode of the image processing unit 8 uses the second variation data as the second fluctuation data. The second variation data is data indicating the variation in the waveform of the second difference data.

In the second mode of the image processing unit 8, the fourth calculation unit defines, as the second variation data, data obtained by calculating a moving standard deviation of the second difference data in units of the fourth predetermined number of frames (e.g., 21) smaller than the K frames, and calculates the M second variation data corresponding to each of the M time-series pixel data (step S6). Instead of the moving standard deviation, moving dispersion may be used.

FIG. 14 is a graph illustrating the first variation data D5 and the second variation data D8. A horizontal axis of the graph is the same as the horizontal axis of the graph of FIG. 2A. A vertical axis of the graph represents a standard deviation. FIG. 14 is a graph obtained by adding the second variation data D8 to the graph illustrated in FIG. 8. The first variation data D5 is data indicating a moving standard deviation of the first difference data D4 illustrated in FIG. 13A. The second variation data D8 is data indicating a moving standard deviation of the second difference data D7 illustrated in FIG. 13B. The number of frames used for calculating the moving standard deviation, which is 21 for both of the first variation data D5 and the second variation data D8, is required at least to be the number that allows calculation of a statistically significant standard deviation, and is not limited to 21.

The first variation data D5 and the second variation data D8, which are standard deviations, do not include negative values. Therefore, the first variation data D5 and the second variation data D8 can be regarded as data obtained by converting the first difference data D4 and the second difference data D7 into absolute values.

The second mode of the image processing unit 8 functions as a fifth calculation unit. The fifth calculation unit defines, as third difference data, data obtained by calculating a difference between the first variation data (one example of the first fluctuation data) and the second variation data (one example of the second fluctuation data) obtained from the same time-series pixel data. The fifth calculation unit extracts the M third difference data corresponding to each of the M time-series pixel data (step S7).

Figure 15:
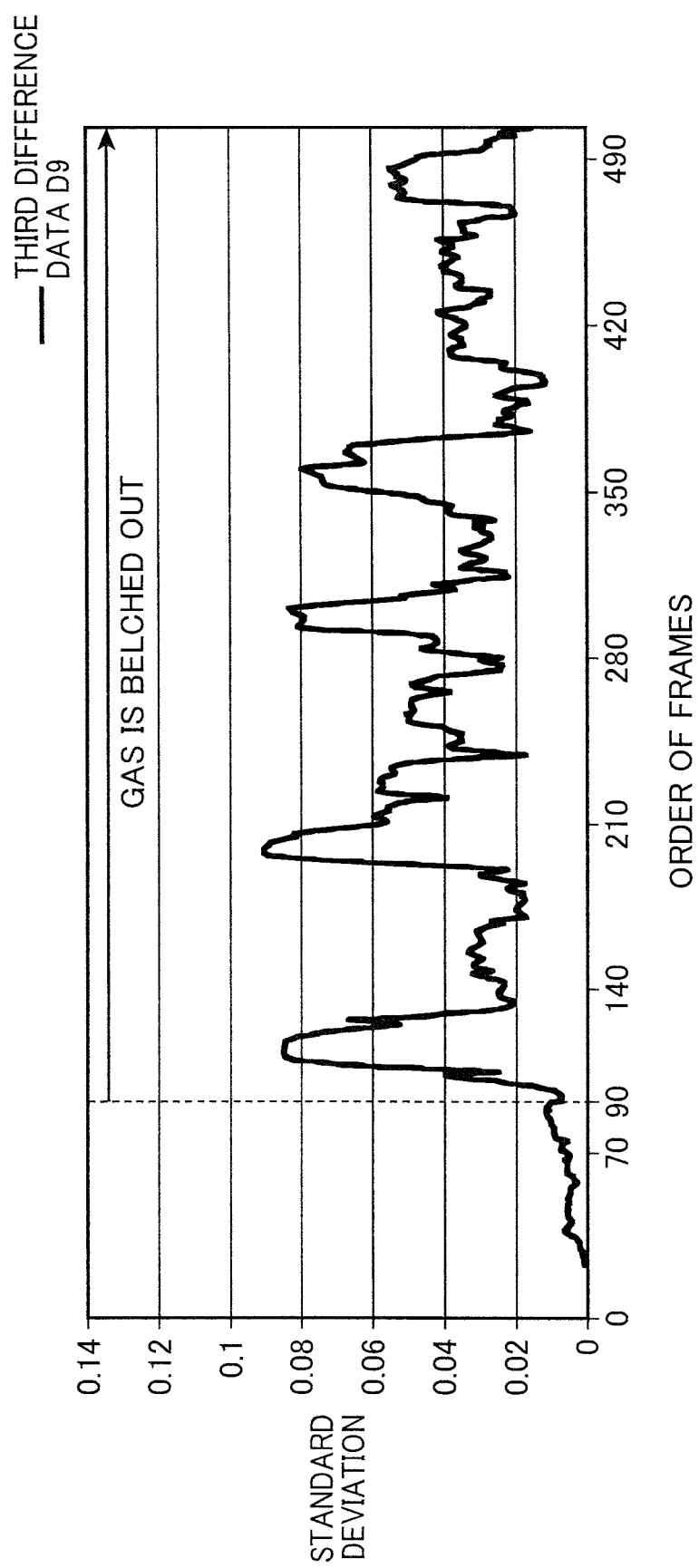
FIG. 15 is a graph illustrating third difference data D9.

FIG. 15 is a graph illustrating the third difference data D9. A horizontal axis of the graph is the same as the horizontal axis of the graph of FIG. 2A. A vertical axis of the graph is a standard deviation. The third difference data D9 is data indicating the difference between the first variation data D5 and the second variation data D8 illustrated in FIG. 14.

Figure 16:
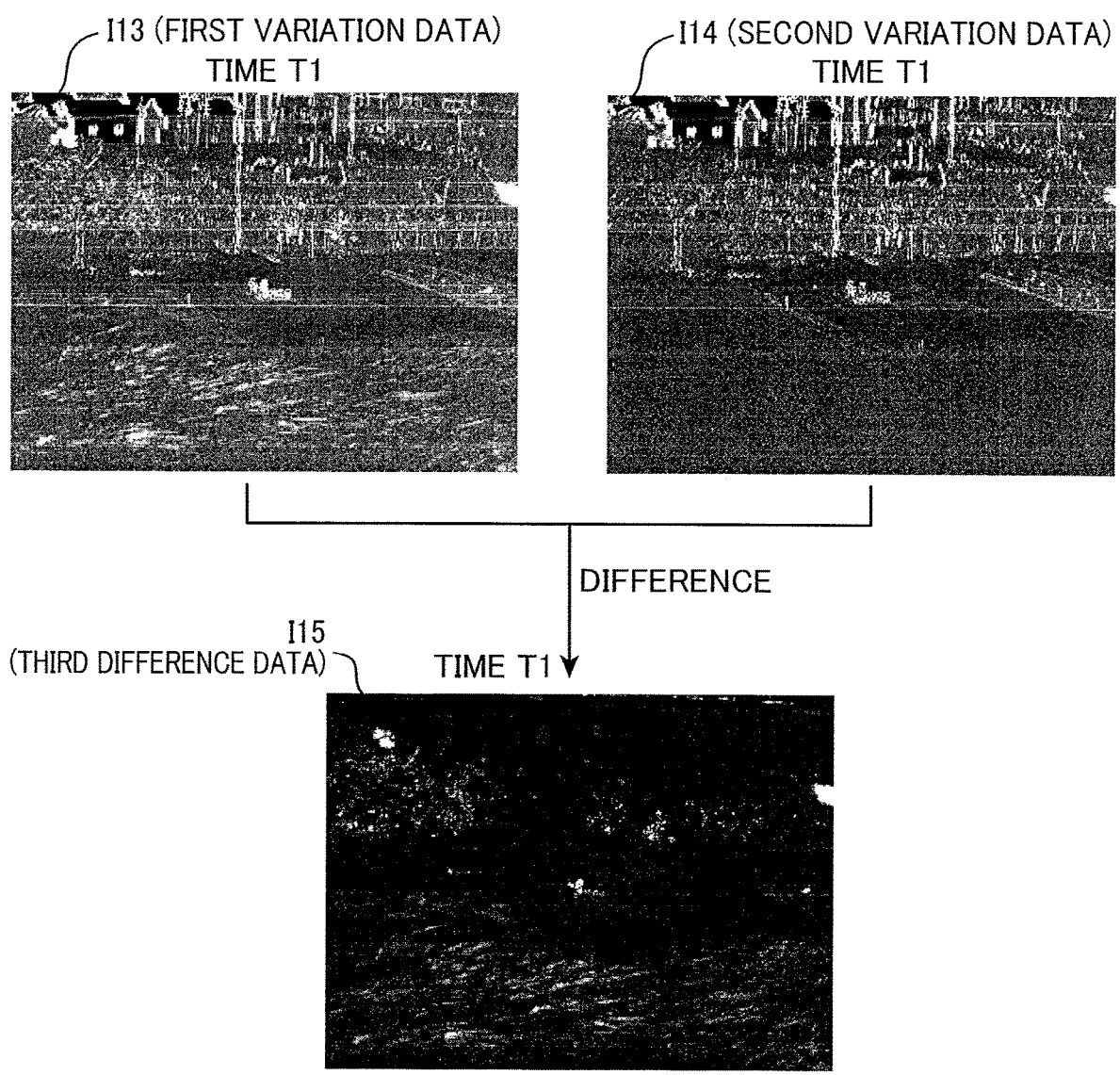
FIG. 16 is an image diagram illustrating an image I15 of a frame at a time T1, and an image I13 and an image I14 related thereto, which have undergone image processing by the second mode of the image processing unit.
Figure 17:
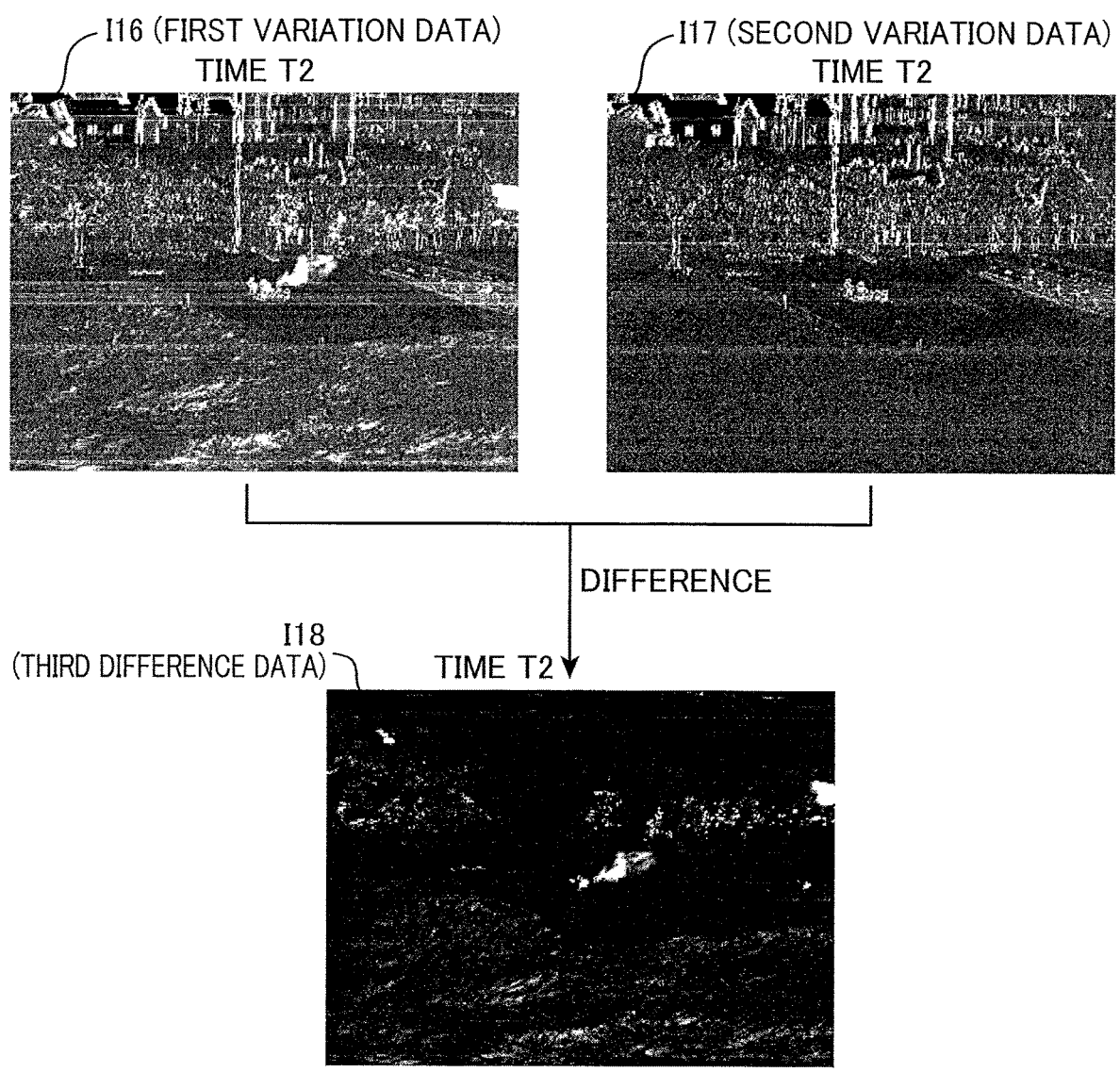
FIG. 17 is an image diagram illustrating an image I18 of a frame at a time T2, and an image I16 and an image I17 related thereto, which have undergone image processing by the second mode of the image processing unit.

The display control unit 9 defines the M third difference data obtained in step S7 as the moving image data D1 that has undergone the process of removing the second frequency component data and the third frequency component data, and causes the display unit 10 to display the moving image indicated by the moving image data D1. In this moving image, FIG. 16 illustrates an image I15 of the frame at the time T1, and an image I13 and an image I14 related thereto, and FIG. 17 illustrates an image I18 of the frame at the time T2, and an image I16 and an image I17 related thereto. Both are images with the standard deviation of 5000.

FIG. 16 is an image diagram illustrating the image I15 of the frame at the time T1, and the image I13 and the image I14 related thereto, processed by the second mode of the image processing unit 8. The image I13 is an image of the frame at the time T1 in the moving image indicated by the M first variation data obtained in step S3 of FIG. 11 (moving image data D1). The image I14 is an image of the frame at the time T1 in the moving image indicated by the M second variation data obtained in step S6 of FIG. 11 (moving image data D1). A difference between the image I13 and the image I14 is the image I15.

FIG. 17 is an image diagram illustrating the image I18 of the frame at the time T2, and the image I16 and the image I17 related thereto, processed by the second mode of the image processing unit 8. The image I16 is an image of the frame at the time T2 in the moving image indicated by the M first variation data obtained in step S3 (moving image data D1). The image I17 is an image of the frame at the time T2 in the moving image indicated by the M second variation data obtained in step S6 (moving image data D1). A difference between the image I16 and the image I17 is the image I18.

Sensor noise, which decreases as the temperature increases, varies with temperature. In the two-dimensional image sensor 6, noise according to the temperature sensed by each pixel occurs in the pixel. That is, the noise of all the pixels is not the same. The second mode of the image processing unit 8, which can remove high-frequency noise from the moving image, can cause the display unit 10 to display even a slight gas leak.

Also, in step S4 of FIG. 11, the second mode of the image processing unit 8 can specify the frequency of the third frequency component data in advance (e.g., 5 Hz or more) and extract the third frequency component data from the time-series pixel data. Therefore, even if the frequencies of the first frequency component data and the third frequency component data are close to each other, only the third frequency component data can be extracted in step S4. This will be described in detail.

Figure 18:
FIG. 18 is an image diagram illustrating an infrared image with a gas being belched out at a spot SP3.
Figure 19:
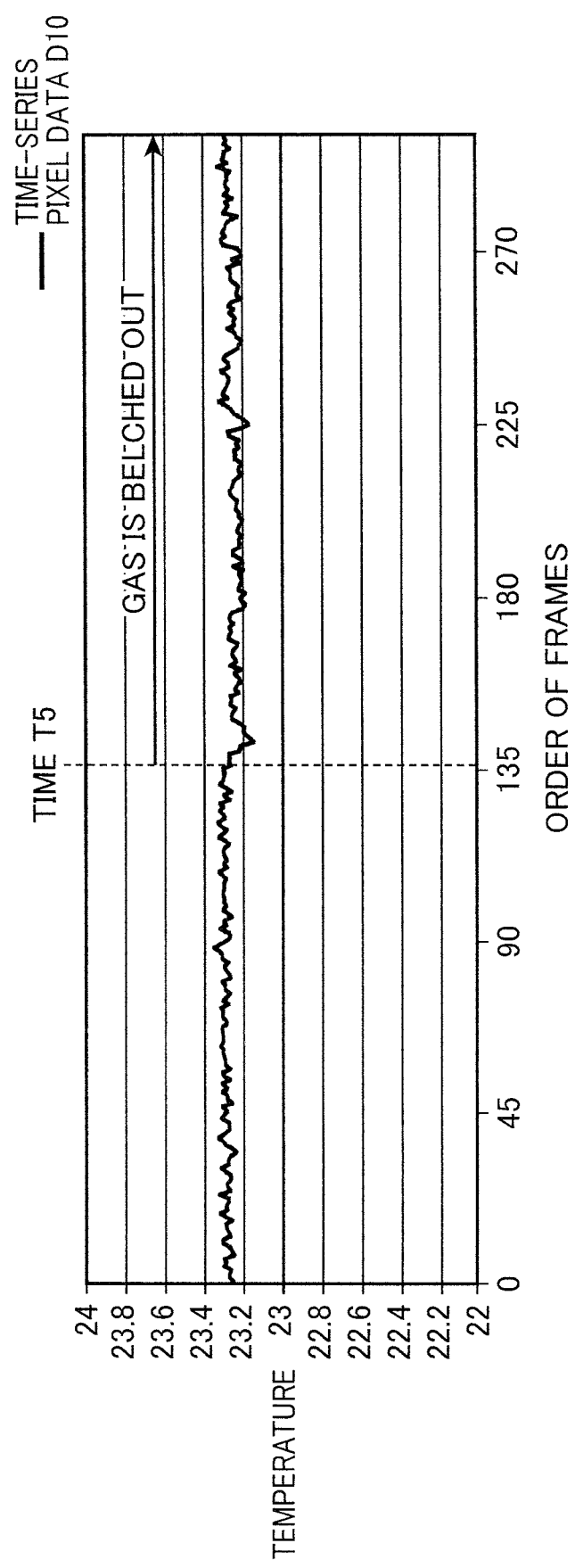
FIG. 19 is a graph illustrating time-series pixel data D10 of a pixel corresponding to the spot SP3.

FIG. 18 is an image diagram illustrating an infrared image I19 with a gas being belched out at a spot SP3. The image processing by the second mode of the image processing unit 8 has not been performed. FIG. 19 is a graph illustrating time-series pixel data D10 of the pixel corresponding to the spot SP3. A vertical axis and a horizontal axis of the graph are the same as the vertical axis and the horizontal axis of the graph of FIG. 2A, respectively. At a time T5, the belch of a gas is started at the spot SP3. No background temperature change occurs. A time T6 at which the infrared image I19 is shot is after the time T5.

The time-series pixel data D10 before the time T5 indicates the third frequency component data. The time-series pixel data D10 after the time T5 indicates data obtained by combining the first frequency component data and the third frequency component data. Since the frequency of the first frequency component data is close to the frequency of the third frequency component data, a large difference does not occur in the waveform of the time-series pixel data before and after the time T5. Therefore, from the infrared image I19 illustrated in FIG. 18, which has not undergone the image processing by the second mode of the image processing unit 8, it is unknown that the gas is being belched out at the spot SP3.

Figure 20:
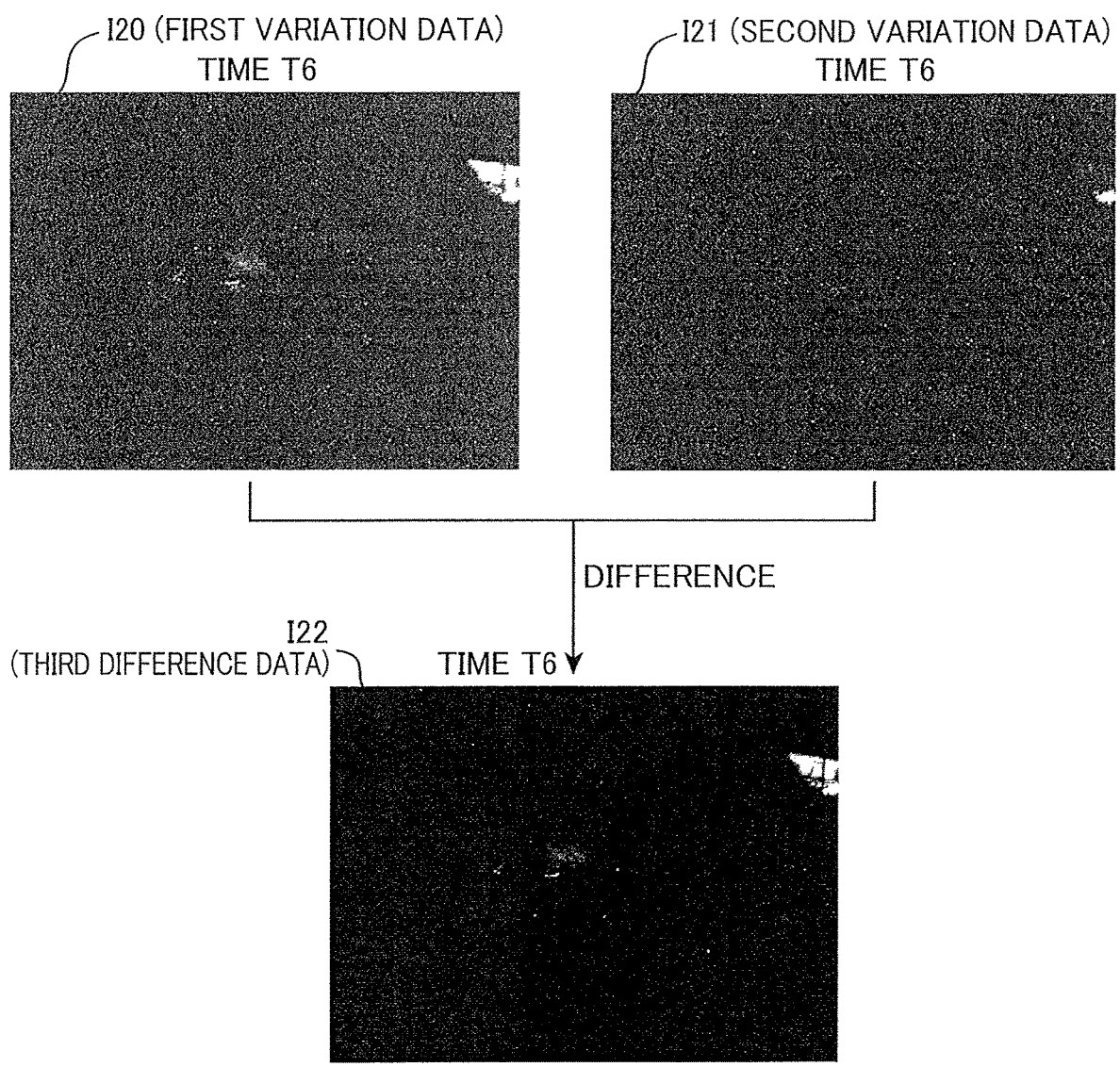
FIG. 20 is an image diagram illustrating an image I22 of a frame at a time T6, and an image I20 and an image I21 related thereto, which have undergone image processing by the second mode of the image processing unit.

FIG. 20 is an image diagram illustrating an image I22 of the frame at the time T6, and an image I20 and an image I21 related thereto, processed by the second mode of the image processing unit 8. The image I20 is an image constituting the moving image indicated by the M first variation data obtained in step S3 of FIG. 11 (moving image data D1). The image I21 is an image constituting the moving image indicated by the M second variation data obtained in step S6 of FIG. 11 (moving image data D1). A difference between the image I20 and the image I21 is the image I22. A white portion at a central portion of the image I22 indicates the belch of a gas.

Figure 21:
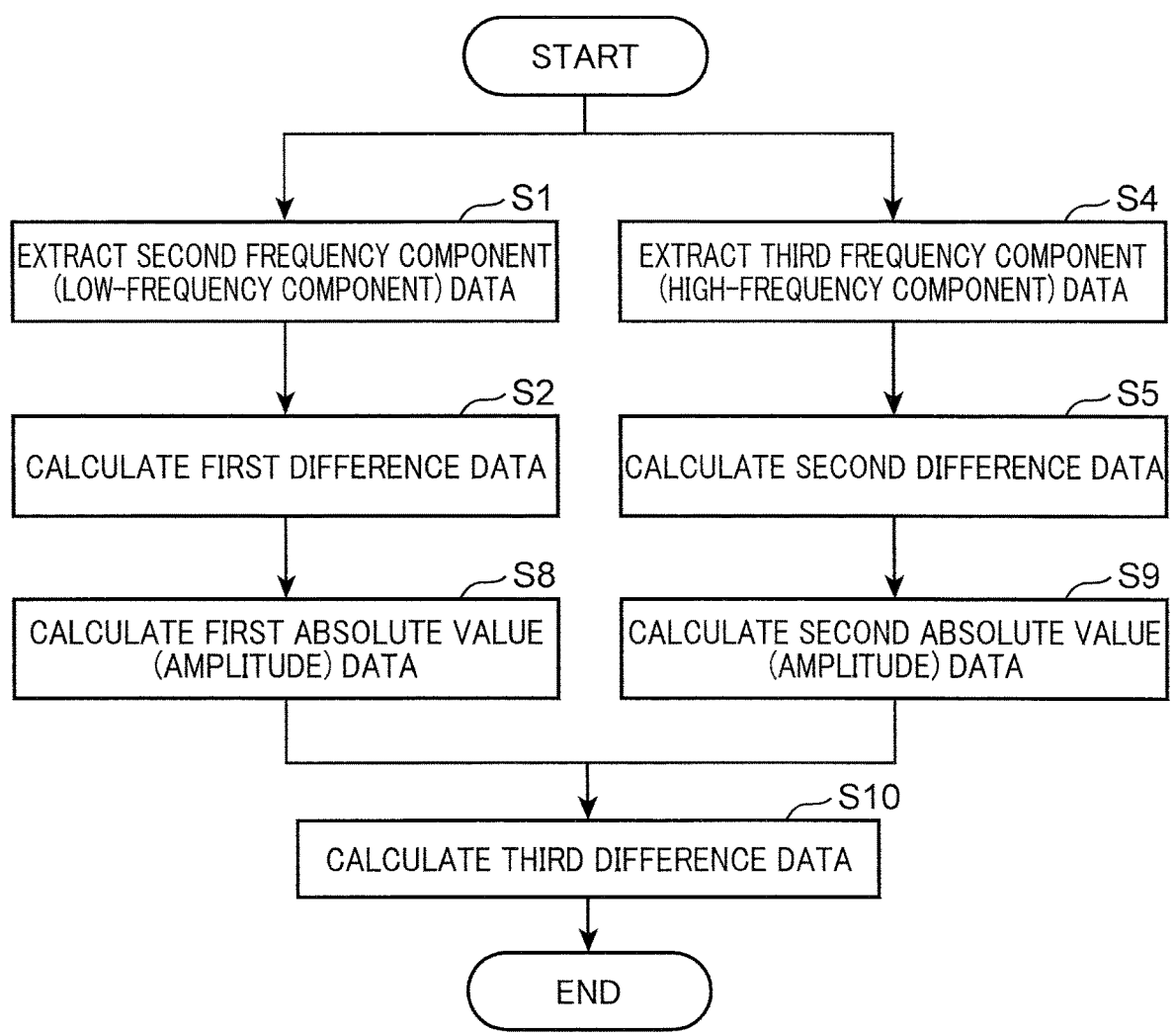
FIG. 21 is a flowchart of a process to be executed by a third mode of the image processing unit.

The third mode of the image processing unit 8 will be described. FIG. 21 is a flowchart of the process to be executed by the third mode of the image processing unit 8. The third mode of the image processing unit 8 differs from the second mode of the image processing unit 8 illustrated in FIG. 11 in that instead of the process of calculating the first variation data (step S3), the process of calculating first absolute value data is performed (step S8), and that instead of the process of calculating the second variation data (step S6), the process of calculating second absolute value data is performed (step S9).

The third mode of the image processing unit 8 functions as the second calculation unit. The second calculation unit defines, as the first absolute value data, data indicating absolute values of the M first difference data obtained in step S2 illustrated in FIG. 21, and calculates the M first absolute value data corresponding to each of the M time-series pixel data illustrated in FIG. 4 (step S8). The third mode of the image processing unit 8 functions as the fourth calculation unit. The fourth calculation unit defines, as the second absolute value data, data indicating absolute values of the M second difference data obtained in step S5 illustrated in FIG. 21, and calculates the M second absolute value data corresponding to each of the M time-series pixel data (step S9).

Figure 22:
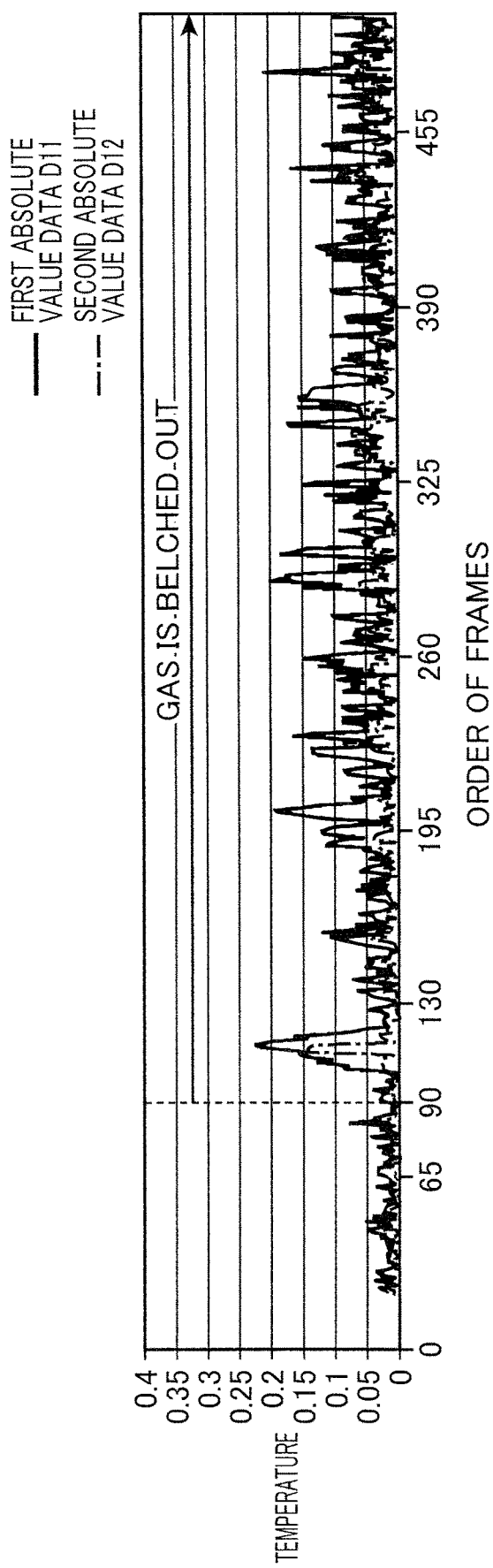
FIG. 22 is a graph illustrating first absolute value data D11 and second absolute value data D12.

FIG. 22 is a graph illustrating the first absolute value data D11 and the second absolute value data D12. A vertical axis and a horizontal axis of the graph are the same as the vertical axis and the horizontal axis of the graph of FIG. 2A, respectively. The first absolute value data D11 is data indicating absolute values of the first difference data D4 illustrated in FIG. 13A. The second absolute value data D12 is data indicating absolute values of the second difference data D7 illustrated in FIG. 13B.

The third mode of the image processing unit 8 functions as the second calculation unit and the fourth calculation unit. The second calculation unit calculates the first absolute value addition data (one example of the first fluctuation data) by performing moving addition on the first absolute value data in units of the second predetermined number of frames smaller than the plurality of frames. The fourth calculation unit calculates the second absolute value addition data (one example of the second fluctuation data) by performing moving addition on the second absolute value data in units of the second predetermined number of frames smaller than the plurality of frames.

Figure 23:
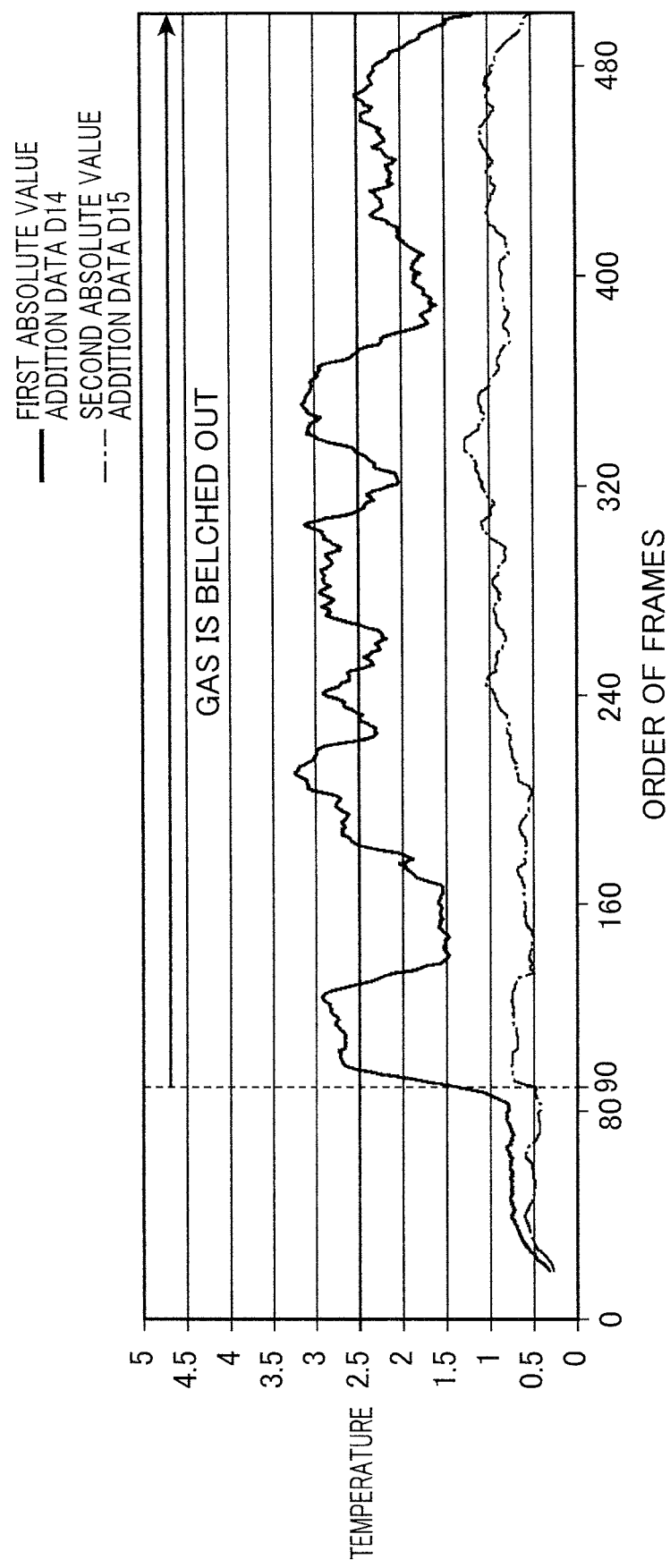
FIG. 23 is a graph illustrating first absolute value addition data D14 and second absolute value addition data D15.
Figure 24:
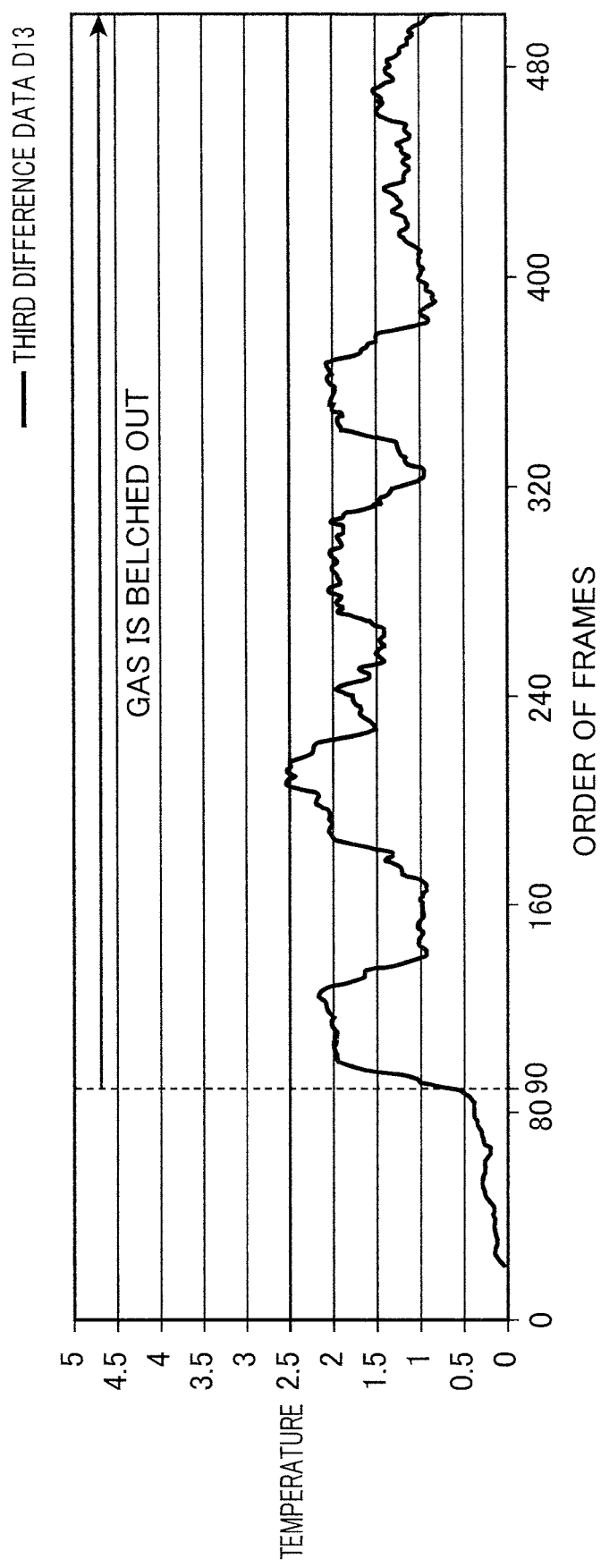
FIG. 24 is a graph illustrating third difference data D13.

FIG. 23 is a graph illustrating the first absolute value addition data D14 and the second absolute value addition data D15. A vertical axis and a horizontal axis of the graph are the same as the vertical axis and the horizontal axis of the graph of FIG. 2A, respectively. The first absolute value addition data D14 is data obtained by performing addition on the first absolute value data D11 illustrated in FIG. 22 in units of the predetermined number of frames (e.g., 21) smaller than the K frames illustrated in FIG. 4. The second calculation unit calculates the M first absolute value addition data corresponding to each of the M time-series pixel data. The second absolute value addition data D15 is data obtained by performing addition on the second absolute value data D12 illustrated in FIG. 22 in units of the predetermined number of frames (e.g., 21) smaller than the K frames. The fourth calculation unit calculates the M second absolute value addition data corresponding to each of the M time-series pixel data. In the simple moving average in units of 21 frames, added values are divided by 21, but in the addition in units of 21 frames, this division process is not performed.

The third mode of the image processing unit 8 functions as the fifth calculation unit. The fifth calculation unit defines, as the third difference data, data obtained by calculating a difference between the first absolute value addition data (one example of the first fluctuation data) and the second absolute value addition data (one example of the second fluctuation data) obtained from the same time-series pixel data. The fifth calculation unit calculates the M third difference data corresponding to each of the M time-series pixel data (step S10).

The display control unit 9 defines the M third difference data obtained in step S10 as the moving image data D1 that has undergone the process of removing the second frequency component data and the third frequency component data, and causes the display unit 10 to display the moving image indicated by this moving image data D1. The third mode of the image processing unit 8, which can remove high-frequency noise from the moving image, can cause the display unit 10 to display even a slight gas leak.

Figure 25:
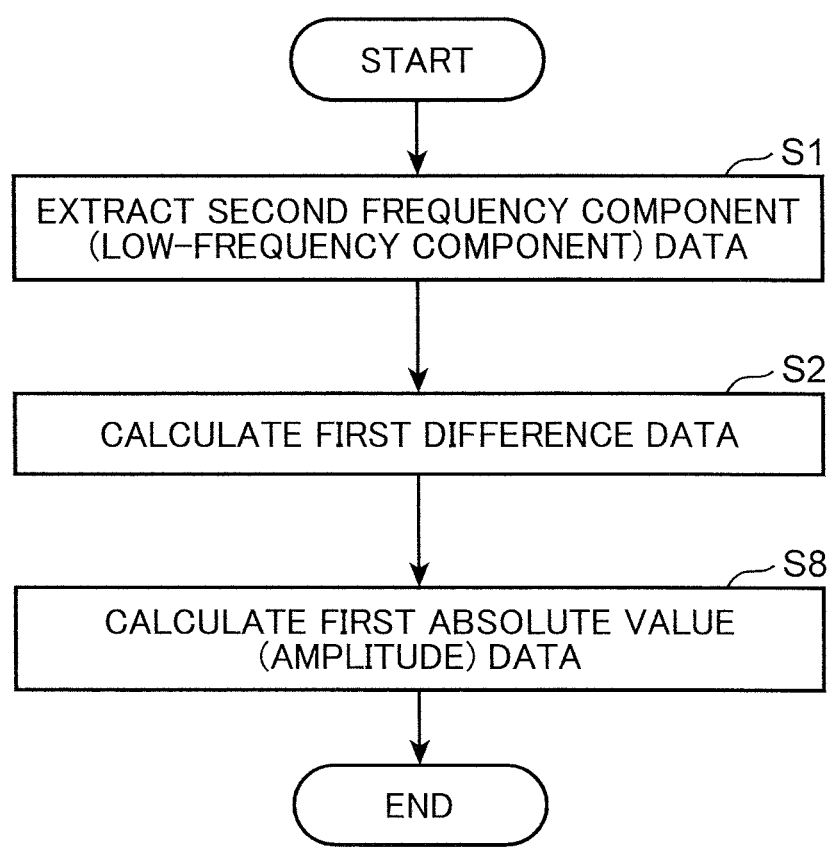
FIG. 25 is a flowchart of a process to be executed by a fourth mode of the image processing unit.

The fourth mode of the image processing unit 8 will be described. FIG. 25 is a flowchart of the process to be executed by the fourth mode of the image processing unit 8. The fourth mode of the image processing unit 8 differs from the third mode of the image processing unit 8 illustrated in FIG. 21 in that the process of step S4, step S5, step S9, and step S10 is not performed. Therefore, in a similar manner to the first mode of the image processing unit 8 illustrated in FIG. 5, the fourth mode of the image processing unit 8 performs the process of removing the second frequency component data without performing the process of removing the third frequency component data. The fourth mode of the image processing unit 8 is one mode of the image processing unit 8 that performs the process of removing the second frequency component data from the moving image data D1.

The fifth mode of the image processing unit 8 will be described. This is one mode of the image processing unit 8 that performs the process of removing the second frequency component data from the moving image data D1. Also, the fifth mode of the image processing unit 8, which can remove high-frequency noise from the moving image, can cause the display unit 10 to display even a slight gas leak.

Figure 26:
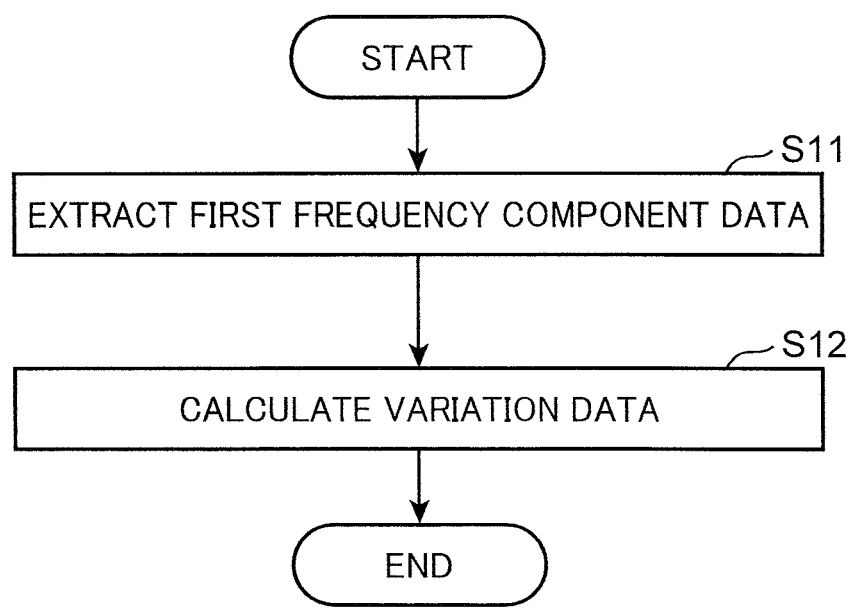
FIG. 26 is a flowchart of a process to be executed by a fifth mode of the image processing unit.

FIG. 26 is a flowchart of the process to be executed by the fifth mode of the image processing unit 8. The fifth mode of the image processing unit 8 extracts the first frequency component data from the time-series pixel data. The first frequency component data is frequency component data indicating the temperature change caused by the leaking gas.

The fifth mode of the image processing unit 8 functions as the extraction unit. By using a weighting coefficient that allows extraction of the first frequency component data, the extraction unit defines, as the first frequency component data, data extracted from the time-series pixel data by calculating a weighted moving average of the time-series pixel data in units of the predetermined number of frames (first predetermined number) smaller than the K frames illustrated in FIG. 4. The first extraction unit extracts the M first frequency component data corresponding to each of the M time-series pixel data illustrated in FIG. 4 (step S11).

Figure 27:
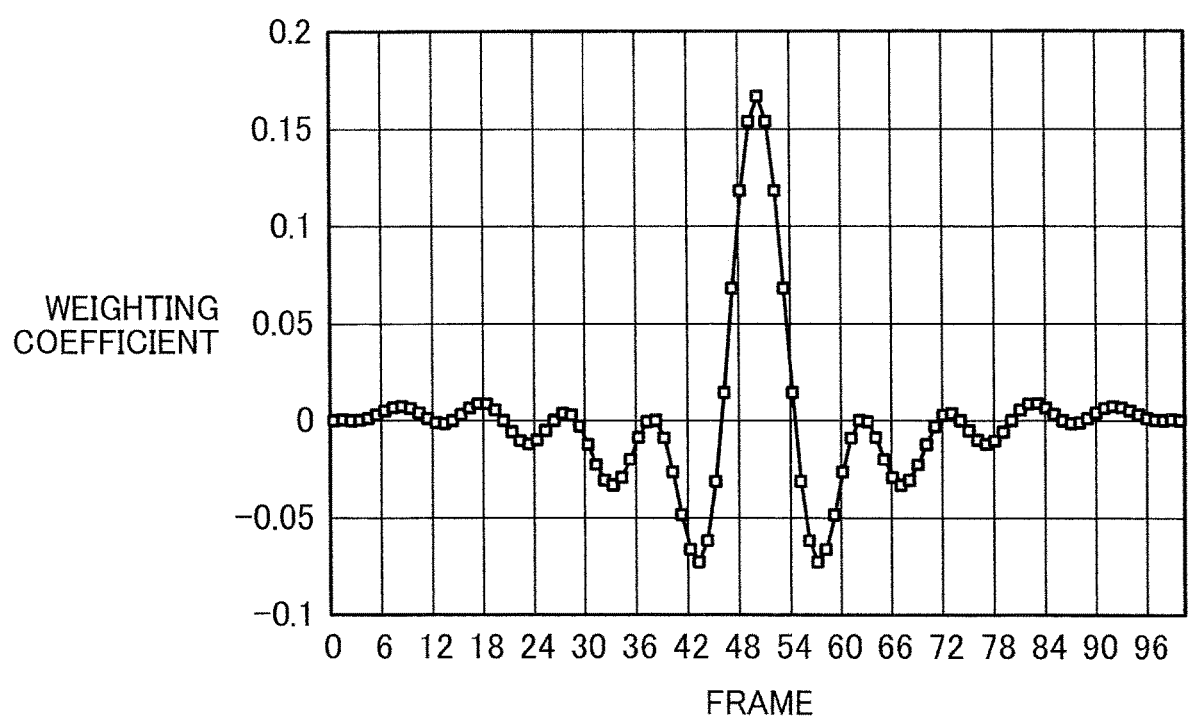
FIG. 27 is an explanatory diagram explaining a band pass filter capable of extracting first frequency component data.

It is assumed that the frequency of the first frequency component data is 0.3 to 3 Hz. FIG. 27 is an explanatory diagram explaining a band pass filter capable of extracting the first frequency component data. A horizontal axis represents the frame, and a vertical axis represents the weighting coefficient. The first predetermined number of frames is, for example, 99 frames. The breakdown is a target frame, 49 consecutive frames before the target frame, and 49 consecutive frames after the target frame. The first predetermined number is required at least to be the number that allows extraction of the first frequency component from the time-series pixel data, and the first predetermined number may be more than 99 or less than 99.

Figure 28:
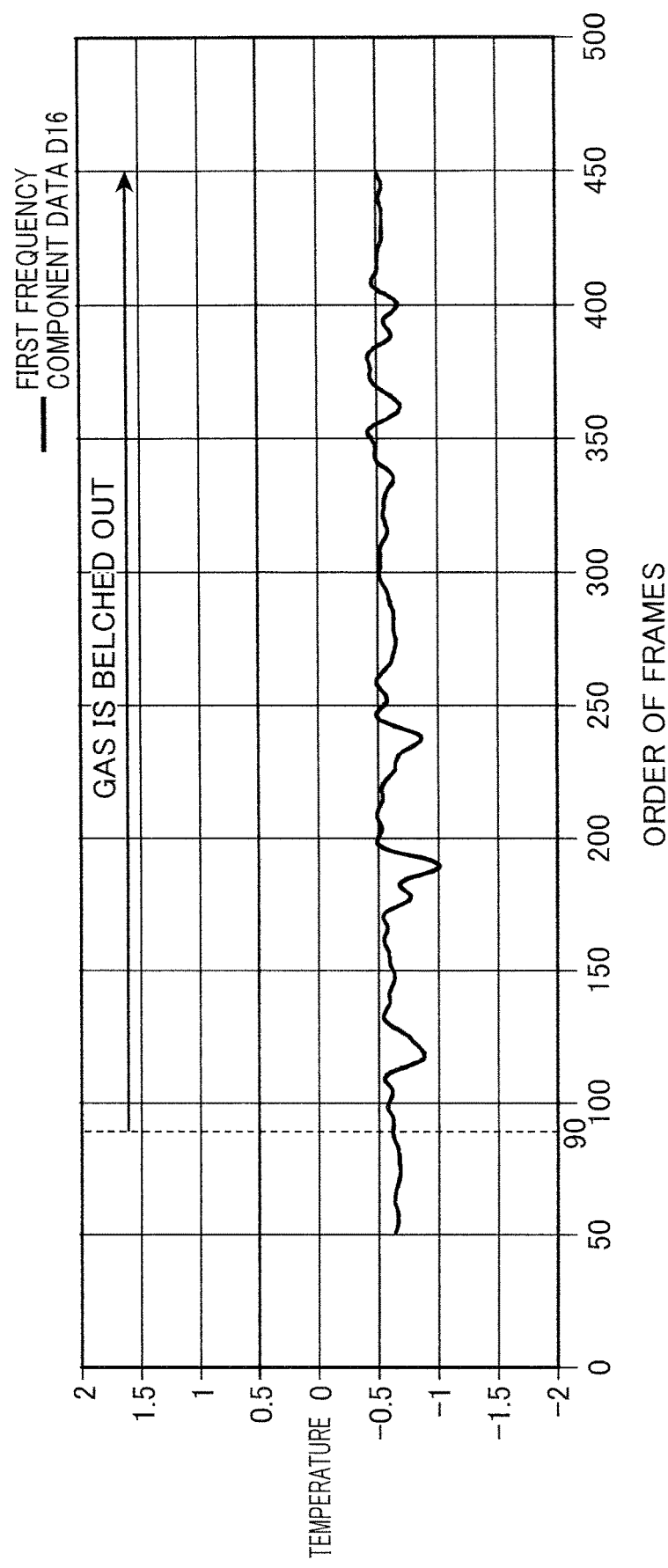
FIG. 28 is a graph illustrating the extracted first frequency component data D16.

FIG. 28 is a graph illustrating the extracted first frequency component data D16. A vertical axis and a horizontal axis of the graph are the same as the vertical axis and the horizontal axis of the graph of FIG. 2A, respectively. The first frequency component data D16 is data extracted from the time-series pixel data of the pixels corresponding to the spot SP1 illustrated in FIG. 2A.

The fifth mode of the image processing unit 8 functions as the calculation unit. The calculation unit defines, as fluctuation data, data indicating a fluctuation in the first frequency component calculated based on the first frequency component data, and calculates the plurality of (M) fluctuation data corresponding to each of the plurality of (M) time-series pixel data. The fifth mode uses the variation data as the fluctuation data. That is, the calculation unit defines, as the variation data, data obtained by calculating a moving standard deviation of the first frequency component data in units of the second predetermined number of frames smaller than the K frames, and calculates the M variation data corresponding to each of the M time-series pixel data (step S12). Note that instead of the moving standard deviation, moving dispersion may be calculated.

Figure 29:
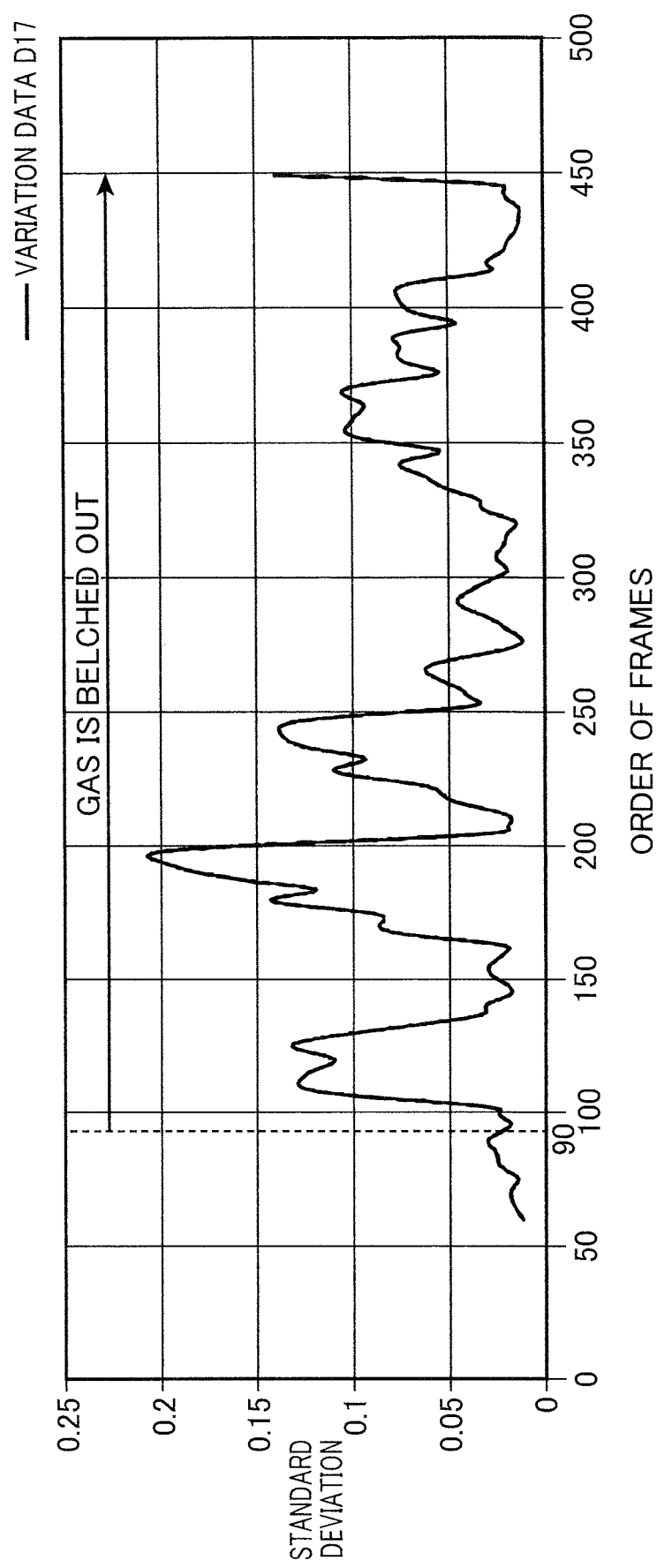
FIG. 29 is a graph illustrating variation data D17.

FIG. 29 is a graph illustrating variation data D17. A horizontal axis of the graph is the same as the horizontal axis of the graph of FIG. 2A. A vertical axis of the graph represents a standard deviation. The variation data D17 is data indicating the moving standard deviation of the first frequency component data D16 illustrated in FIG. 28. The second predetermined number of frames is, for example, 21 frames. The second predetermined number, which is 21, is required at least to be the number that allows calculation of a statistically significant standard deviation, and is not limited to 21.

The display control unit 9 defines the M variation data obtained in step S12 as the moving image data D1 that has undergone the process of removing the second frequency component data and the third frequency component data. The display control unit 9 causes the display unit 10 to display the moving image indicated by the moving image data D1.

The sixth mode of the image processing unit 8 will be described. This is one mode of the image processing unit 8 that performs the process of removing the second frequency component data from the moving image data D1. Also, the sixth mode of the image processing unit 8, which can remove high-frequency noise from the moving image, can cause the display unit 10 to display even a slight gas leak.

To the flowchart of the process to be executed by the sixth mode of the image processing unit 8, the flowchart of the process to be executed by the second mode of the image processing unit 8 illustrated in FIG. 11 can be applied, and the flowchart of the process to be executed by the third mode of the image processing unit 8 illustrated in FIG. 21 can also be applied. The sixth mode of the image processing unit 8 collectively performs the process of step S1 and the process of step S2, and collectively performs the process of step S4 and the process of step S5.

The sixth mode of the image processing unit 8 functions as the first calculation unit. By using a weighting coefficient that allows extraction of the second frequency component data, the first calculation unit defines, as the first difference data, data obtained by calculating a weighted moving average of the time-series pixel data in units of the first predetermined number of frames smaller than the K frames illustrated in FIG. 4. The first difference data is a difference between the time-series pixel data and the second frequency component data. The first calculation unit calculates the M first difference data corresponding to each of the M time-series pixel data (process in which the process of step S1 and the process of step S2 are combined).

The sixth mode of the image processing unit 8 functions as the third calculation unit. The third calculation unit defines, as the third frequency component data, data indicating high-frequency noise, the data being higher in frequency than the first frequency component data. By using a weighting coefficient that allows extraction of the third frequency component data, the third calculation unit defines, as the second difference data, data obtained by calculating a weighted moving average of the time-series pixel data in units of the third predetermined number of frames smaller than the K frames. The second difference data is a difference between the time-series pixel data and the third frequency component data. The third calculation unit calculates the M second difference data corresponding to each of the M time-series pixel data (process in which the process of step S4 and the process of step S5 are combined).

Figure 30:
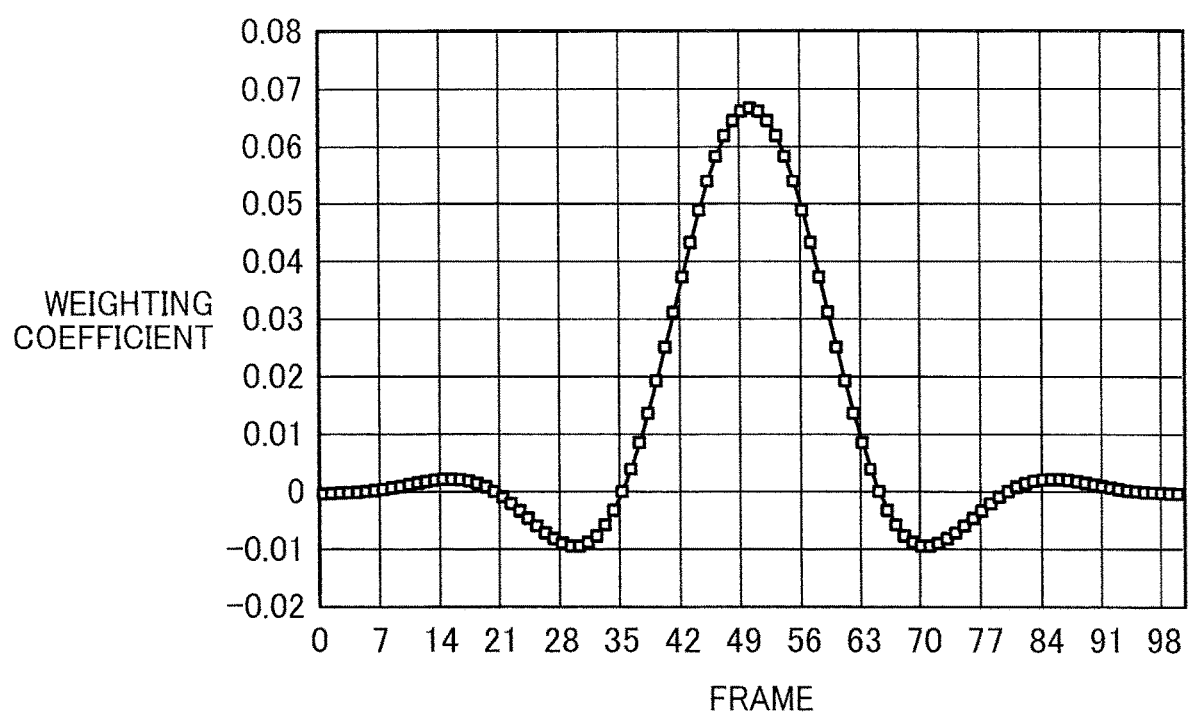
FIG. 30 is an explanatory diagram explaining a filter capable of extracting the first difference data.
Figure 31:
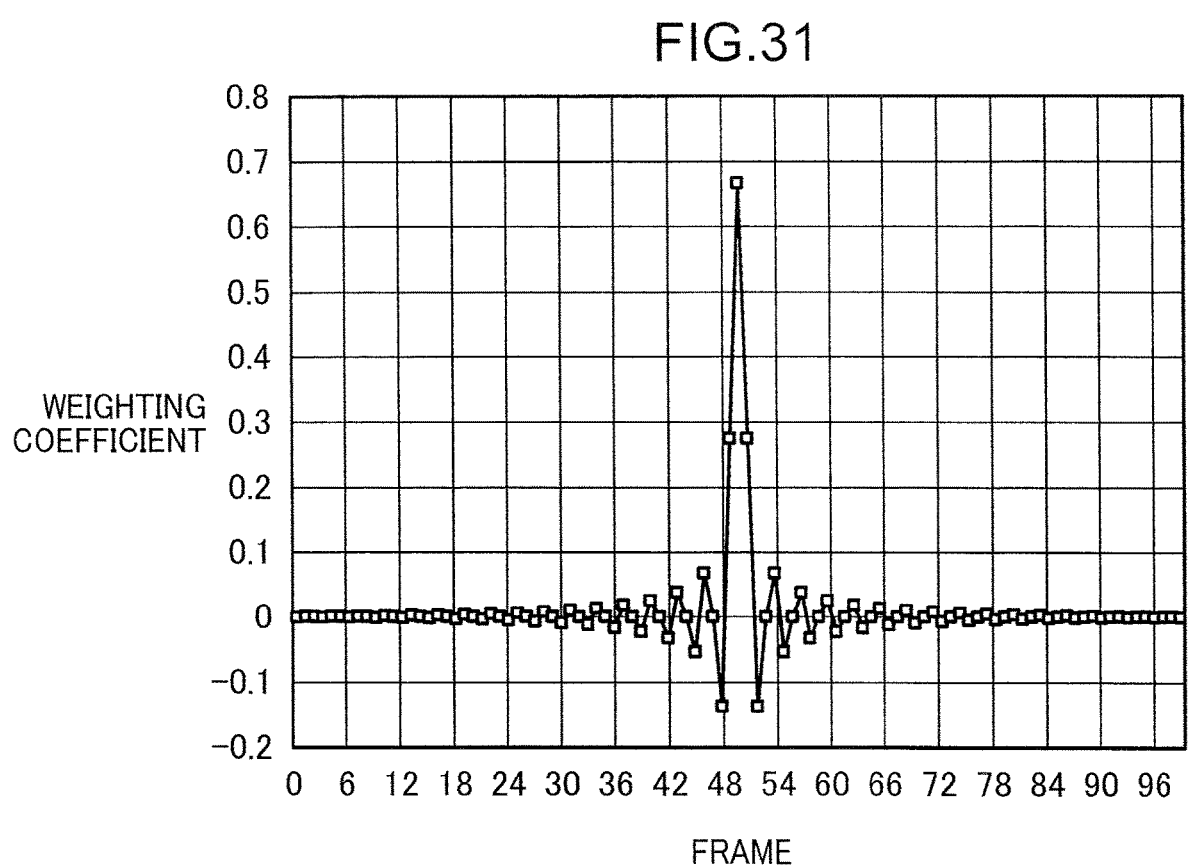
FIG. 31 is an explanatory diagram explaining a filter capable of extracting the second difference data.

It is assumed that the frequency of the second frequency component data is 0.5 Hz or less, and that the frequency of the third frequency component data is 5 Hz or more. FIG. 30 is an explanatory diagram explaining a filter capable of extracting the first difference data. FIG. 31 is an explanatory diagram explaining a filter capable of extracting the second difference data. Horizontal axes of FIGS. 30 and 31 represent frames, and vertical axes represent weighting coefficients. The first predetermined number and the third predetermined number of frames are, for example, 99 frames. The breakdown is a target frame, 49 consecutive frames before the target frame, and 49 consecutive frames after the target frame.

The subsequent process to be executed by the sixth mode of the image processing unit 8 is the same as the process of step S3, step S6, and step S7 when the flowchart illustrated in FIG. 11 is applied, and is the same as the process of step S8, step S9, and step S10 when the flowchart illustrated in FIG. 21 is applied.

The sixth mode of the image processing unit 8 has a modification. The modification includes the first calculation unit described above, but does not include the third calculation unit. To the flowchart of the process to be executed by the modification, the flowchart of the process to be executed by the first mode of the image processing unit 8 illustrated in FIG. 5 can be applied, and the flowchart of the process to be executed by the fourth mode of the image processing unit 8 illustrated in FIG. 25 can also be applied. In the modification, the process of step S1 and the process of step S2 are collectively performed. The subsequent process is the same as the process of step S3 when the flowchart illustrated in FIG. 5 is applied, and is the same as the process of step S8 when the flowchart illustrated in FIG. 25 is applied.

The seventh mode of the image processing unit 8 will be described. This is one mode of the image processing unit 8 that performs the process of removing the second frequency component data from the moving image data D1. Also, the seventh mode of the image processing unit 8, which can remove high-frequency noise from the moving image, can cause the display unit 10 to display even a slight gas leak.

Figure 32:
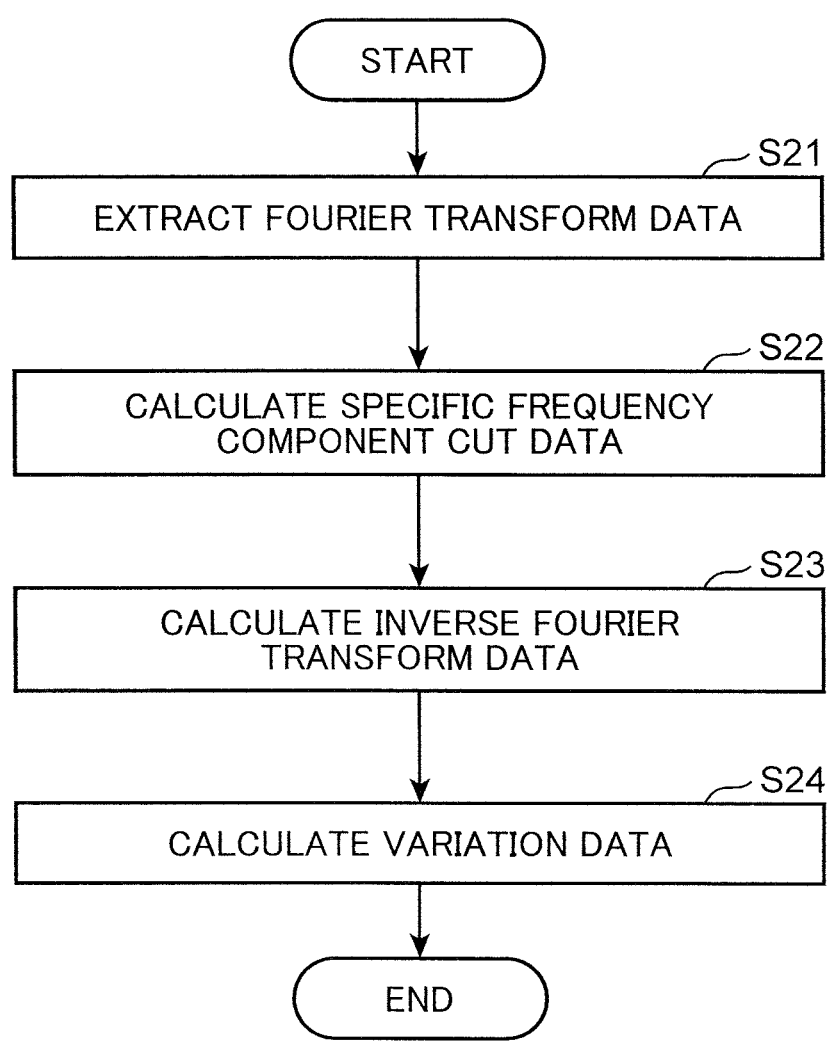
FIG. 32 is a flowchart of a process to be executed by a seventh mode of the image processing unit.

FIG. 32 is a flowchart of the process to be executed by the seventh mode of the image processing unit 8. The seventh mode of the image processing unit 8 removes the second frequency component data and the third frequency component data from the time-series pixel data, by using Fourier transform and inverse Fourier transform.

The seventh mode of the image processing unit 8 functions as the first calculation unit. The first calculation unit defines data obtained by performing Fourier transform on the time-series pixel data as Fourier transformed data, and calculates the M Fourier transformed data corresponding to each of the M time-series pixel data illustrated in FIG. 4 (step S21).

The seventh mode of the image processing unit 8 functions as the second calculation unit. The second calculation unit defines, as specific frequency component cut data, data obtained by removing the second frequency component data and the third frequency component data from the Fourier transformed data, and calculates the M specific frequency component cut data corresponding to each of the M time-series pixel data (step S22). Here, it is assumed that the frequency of the second frequency component data is, for example, 0.5 Hz or less, and that the frequency of the third frequency component data is, for example, 5 Hz or more.

Figure 33:
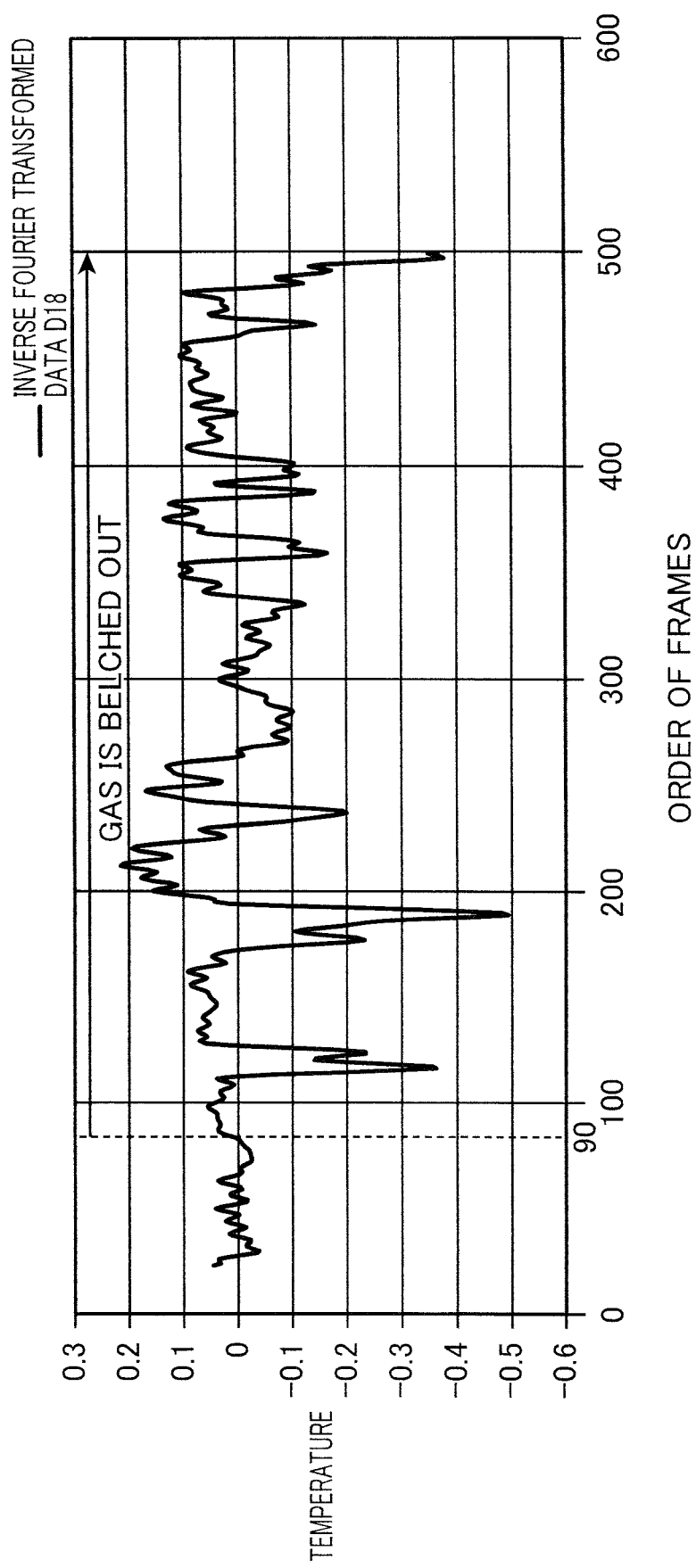
FIG. 33 is a graph illustrating inverse Fourier transformed data D18.

The seventh mode of the image processing unit 8 functions as the third calculation unit. The third calculation unit defines, as inverse Fourier transformed data, data obtained by performing inverse Fourier transform on the specific frequency component cut data, and calculates the M inverse Fourier transformed data corresponding to each of the M time-series pixel data (step S23). FIG. 33 is a graph illustrating the inverse Fourier transformed data D18. A vertical axis and a horizontal axis of the graph are the same as the vertical axis and the horizontal axis of the graph of FIG. 2A, respectively. The inverse Fourier transformed data D18 is data calculated from the time-series pixel data of the pixels corresponding to the spot SP1 illustrated in FIG. 2A. FIG. 33 illustrates a result of performing the process of step S21, step S22, and step S23 with the frame number K of 512.

The seventh mode of the image processing unit 8 functions as the fourth calculation unit. The fourth calculation unit defines, as fluctuation data, data indicating a fluctuation in the inverse Fourier transformed data obtained based on the inverse Fourier transformed data, and calculates the plurality of fluctuation data corresponding to each of the plurality of inverse Fourier transformed data. The seventh mode uses the variation data as the fluctuation data. That is, the fourth calculation unit defines, as the variation data, data obtained by calculating a moving standard deviation of the inverse Fourier transformed data in units of the predetermined number of frames smaller than the K frames, and calculates the M variation data corresponding to each of the M inverse Fourier transformed data (step S24). Note that instead of the moving standard deviation, moving dispersion may be calculated.

Figure 34:
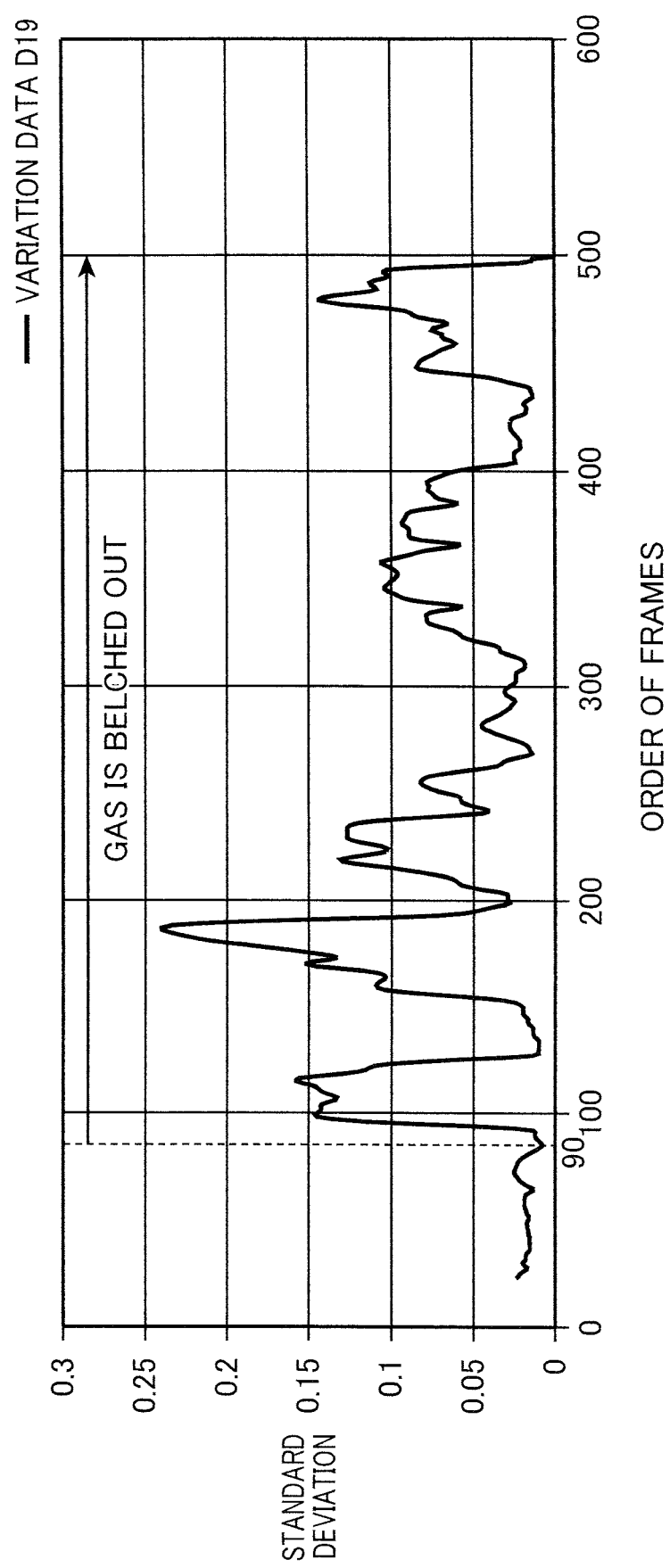
FIG. 34 is a graph illustrating variation data D19.

FIG. 34 is a graph illustrating variation data D19. A horizontal axis of the graph is the same as the horizontal axis of the graph of FIG. 2A. A vertical axis of the graph represents a standard deviation. The variation data D19 is data indicating a moving standard deviation of the inverse Fourier transformed data D18 illustrated in FIG. 33. The predetermined number of frames is, for example, 21 frames. The predetermined number is 21, but is required at least to be a number that allows calculation of a statistically significant standard deviation, and is not limited to 21.

The display control unit 9 defines the M variation data obtained in step S24 as the moving image data D1 that has undergone the process of removing the second frequency component data and the third frequency component data, and causes the display unit 10 to display the moving image indicated by the moving image data D1.

In the image processing device for gas detection 3 according to the present embodiment illustrated in FIG. 3A, the image processing unit 8 performs image processing that can indicate how a gas is leaking as an image, and the display control unit 8 causes the display unit 10 to display the image that has undergone the image processing. The present invention is not limited to this configuration, and may be a configuration that includes the image processing unit 8 but does not include the display control unit 9 and the display unit 10, or may be a configuration that includes the image processing unit 8 and the display control unit 9 but does not include the display unit 10.

Conclusion of Embodiment

An image processing device for gas detection according to the first aspect the present embodiment for achieving the object described above is an image processing device for gas detection for performing image processing on infrared images obtained by shooting an object to be monitored for a gas leak at a plurality of time points, the image processing device for gas detection including: an image processing unit configured to perform a process of removing, from image data indicating the infrared images, second frequency component data lower in frequency than first frequency component data indicating a temperature change caused by the leaking gas, the second frequency component data indicating a background temperature change of the object to be monitored.

While the infrared images to be monitored for a gas leak are being shot at a plurality of time points, when the gas leak occurs, the image data includes the first frequency component data indicating the temperature change caused by the leaking gas. Among the infrared images, the image indicated by the first frequency component data indicates how the gas is leaking (in other words, a region where the leaking gas is drifting).

The inventors have found out the following phenomenon. While the infrared images to be monitored for a gas leak are shot at a plurality of time points, when the gas leak and the background temperature change to be monitored occur in parallel and the background temperature change is larger than the temperature change caused by the leaking gas, it is unknown from the infrared images how the gas is leaking. This is because, in addition to the first frequency component data, the image data includes the second frequency component data that is lower in frequency than the first frequency component data and indicates the background temperature change. An image indicated by the first frequency component data becomes invisible due to an image indicated by the second frequency component data (change in contrast between light and shade of the background).

In the image processing device for gas detection according to the first aspect of the present embodiment, the image processing unit performs the process of removing the second frequency component data included in the image data. Therefore, even when the gas leak and the background temperature change occur in parallel and the background temperature change is larger than the temperature change caused by the leaking gas, the image processing device for gas detection according to the first aspect of the present embodiment can perform image processing that can indicate as an image how the gas is leaking.

In the configuration described above, the image processing unit performs a process of removing, from the image data, third frequency component data higher in frequency than the first frequency component data, the third frequency component data indicating high-frequency noise.

With this configuration, since the high-frequency noise can be removed from the image data, it is possible to perform image processing that can indicate as an image how the gas is slightly leaking.

In the configuration described above, the image data is moving image data having a structure in which a plurality of frames is arranged on a time-series basis, and the image processing unit defines, as time-series pixel data, data obtained by arranging pixel data of pixels at identical positions of the plurality of frames on a time-series basis, the image processing unit performing a process of removing the second frequency component data from each of a plurality of the time-series pixel data constituting the moving image data.

With this configuration, the process of removing the second frequency component data is not performed in units of the frames, but the process of removing the second frequency component data is performed in units of the time-series pixel data. The time-series pixel data is data obtained by arranging pixel data of pixels at identical positions of the plurality of frames on a time-series basis. The number of time-series pixel data is the same as the number of pixels constituting one frame, and the moving image data include the plurality of the time-series pixel data.

The image processing device for gas detection according to the first aspect of the present embodiment can be divided into the following three technical ideas. The first is a technical idea of removing, from the image data, the second frequency component data, or the second frequency component data and the third frequency component data. The second is a technical idea of extracting the first frequency component data from the image data. The third is a technical idea of using Fourier transform.

The first technical idea is as follows.

The image processing unit includes: a first extraction unit that defines, as the second frequency component data, data extracted by performing a first predetermined process on the time-series pixel data, the first extraction unit extracting a plurality of the second frequency component data corresponding to each of the plurality of the time-series pixel data; and a first calculation unit that defines, as first difference data, data obtained by calculating a difference between the time-series pixel data and the second frequency component data extracted from the time-series pixel data, the first calculation unit calculating a plurality of the first difference data corresponding to each of the plurality of the time-series pixel data. This corresponds to the first to fourth modes of the image processing unit.

The first predetermined process is a process of extracting the second frequency component data from the time-series pixel data by calculating a moving average of the time-series pixel data in units of a first predetermined number of the frames smaller than the plurality of frames. This corresponds to the first to fourth modes of the image processing unit.

The image processing unit includes a first calculation unit that defines, as first difference data, data obtained by calculating a weighted moving average of the time-series pixel data in units of a first predetermined number of the frames smaller than the plurality of frames, by using a weighting coefficient that allows extraction of the second frequency component data, the first difference data being a difference between the time-series pixel data and the second frequency component data, and the first calculation unit calculating a plurality of the first difference data corresponding to each of the plurality of the time-series pixel data. This corresponds to the sixth mode of the image processing unit.

The image processing unit further includes a second calculation unit that defines, as first fluctuation data, data indicating a fluctuation in the first difference data, the data being calculated by performing a predetermined operation on the first difference data in units of a second predetermined number of the frames, the second calculation unit calculating a plurality of the first fluctuation data corresponding to each of the plurality of the time-series pixel data. This corresponds to the first to fourth modes and the sixth mode of the image processing unit.

The first fluctuation data is first variation data, and the second calculation unit calculates the first variation data by calculating one of a moving standard deviation and moving dispersion of the first difference data in units of the second predetermined number of the frames smaller than the plurality of frames. This corresponds to the first, second, and sixth modes of the image processing unit.

The first fluctuation data is first absolute value addition data, the second calculation unit defines, as first absolute value data, data indicating an absolute value of the first difference data obtained based on the first difference data, and the second calculation unit calculates the first absolute value addition data by performing moving addition on the first absolute value data in units of the second predetermined number of the frames smaller than the plurality of frames. This corresponds to the third, fourth, and sixth modes of the image processing unit.

The image processing unit includes: a second extraction unit that defines, as third frequency component data, data extracted by performing a second predetermined process on the time-series pixel data, the third frequency component data being data higher in frequency than the first frequency component data, the data indicating high-frequency noise, the second extraction unit extracting a plurality of the third frequency component data corresponding to each of the plurality of the time-series pixel data; a third calculation unit that defines, as second difference data, data obtained by calculating a difference between the time-series pixel data and the third frequency component data extracted from the time-series pixel data, the third calculation unit calculating a plurality of the second difference data corresponding to each of the plurality of the time-series pixel data; a fourth calculation unit that defines, as second fluctuation data, data indicating a fluctuation in the second difference data, the data being calculated by performing a predetermined operation on the second difference data in units of a fourth predetermined number of the frames, the fourth calculation unit calculating a plurality of the second fluctuation data corresponding to each of the plurality of the time-series pixel data; and a fifth calculation unit that defines, as third difference data, data obtained by calculating a difference between the first fluctuation data and the second fluctuation data obtained from the same time-series pixel data, the fifth calculation unit calculating a plurality of the third difference data corresponding to each of the plurality of the time-series pixel data. This corresponds to the second and third modes of the image processing unit.

The second predetermined process is a process of extracting the third frequency component data from the time-series pixel data by calculating a moving average of the time-series pixel data in units of a third predetermined number of the frames. This corresponds to the second and third modes of the image processing unit. The third predetermined number is, for example, less than the first predetermined number.

The image processing unit includes: a third calculation unit that defines, as third frequency component data, data higher in frequency than the first frequency component data, the data indicating high-frequency noise, the third calculation unit defining, as second difference data, data obtained by calculating a weighted moving average of the time-series pixel data in units of a third predetermined number of the frames smaller than the plurality of frames by using a weighting coefficient that allows extraction of the third frequency component data, the second difference data being a difference between the time-series pixel data and the third frequency component data, the third calculation unit calculating a plurality of the second difference data corresponding to each of the plurality of the time-series pixel data; a fourth calculation unit that defines, as second fluctuation data, data indicating a fluctuation in the second difference data, the data being calculated by performing a predetermined operation on the second difference data in units of a fourth predetermined number of the frames, the fourth calculation unit calculating a plurality of the second fluctuation data corresponding to each of the plurality of the time-series pixel data; and a fifth calculation unit that defines, as third difference data, data obtained by calculating a difference between the first fluctuation data and the second fluctuation data obtained from the same time-series pixel data, the fifth calculation unit calculating a plurality of the third difference data corresponding to each of the plurality of the time-series pixel data. This corresponds to the sixth mode of the image processing unit.

The second fluctuation data is second variation data, and the fourth calculation unit calculates the second variation data by calculating one of a moving standard deviation and moving dispersion of the second difference data in units of the fourth predetermined number of the frames smaller than the plurality of frames. This corresponds to the second and sixth modes of the image processing unit.

The second fluctuation data is second absolute value addition data, and the fourth calculation unit defines, as second absolute value data, data indicating an absolute value of the second difference data, the data being obtained based on the second difference data, the fourth calculation unit calculating the second absolute value addition data by performing moving addition on the second absolute value data in units of the fourth predetermined number of the frames smaller than the plurality of frames. This corresponds to the third and sixth modes of the image processing unit.

The second technical idea is as follows.

The image processing unit includes: an extraction unit that defines, as the first frequency component data, data extracted from the time-series pixel data by calculating a weighted moving average of the time-series pixel data in units of a predetermined number of the frames smaller than the plurality of frames by using a weighting coefficient that allows extraction of the first frequency component data, the extraction unit extracting a plurality of the first frequency component data corresponding to each of the plurality of the time-series pixel data; and a calculation unit that defines, as fluctuation data, data indicating a fluctuation in the first frequency component, the data being obtained based on the first frequency component data, the calculation unit calculating a plurality of the fluctuation data corresponding to each of the plurality of the time-series pixel data. This corresponds to the fifth mode of the image processing unit.

The third technical idea is as follows.

The image processing unit includes: a first calculation unit that defines data obtained by performing Fourier transform on the time-series pixel data as Fourier transformed data, the first calculation unit calculating a plurality of Fourier transformed data corresponding to each of the plurality of the time-series pixel data; a second calculation unit that defines, as specific frequency component cut data, data obtained by removing the second frequency component data from the Fourier transformed data, the second calculation unit calculating a plurality of the specific frequency component cut data corresponding to each of the plurality of the time-series pixel data; a third calculation unit that defines, as inverse Fourier transformed data, data obtained by performing inverse Fourier transform on the specific frequency component cut data, the third calculation unit calculating a plurality of the inverse Fourier transformed data corresponding to each of the plurality of the time-series pixel data; and a fourth calculation unit that defines, as fluctuation data, data indicating a fluctuation in the inverse Fourier transformed data, the data being obtained based on the inverse Fourier transformed data, the fourth calculation unit calculating a plurality of the fluctuation data corresponding to each of the plurality of the inverse Fourier transformed data. This corresponds to the seventh mode of the image processing unit.

The second calculation unit defines, as the specific frequency component cut data, data obtained by removing, from the Fourier transformed data, third frequency component data that is higher in frequency than the first frequency component data and indicates high-frequency noise, and the second frequency component data, the second calculation unit calculating the plurality of the specific frequency component cut data corresponding to each of the plurality of the time-series pixel data. This corresponds to the seventh mode of the image processing unit.

An image processing method for gas detection according to the second aspect the present embodiment includes: a first step of acquiring image data indicating infrared images obtained by shooting an object to be monitored for a gas leak at a plurality of time points; and a second step of performing a process of removing, from the image data, second frequency component data lower in frequency than first frequency component data indicating a temperature change caused by the leaking gas, the second frequency component data indicating a background temperature change of the object to be monitored.

The image processing method for gas detection according to the second aspect of the present embodiment has the same operational effect as the image processing device for gas detection according to the first aspect of the present embodiment.

An image processing program for gas detection according to the third aspect of the present embodiment causes a computer to execute: a first step of acquiring image data indicating infrared images obtained by shooting an object to be monitored for a gas leak at a plurality of time points; and a second step of performing a process of removing, from the image data, second frequency component data lower in frequency than first frequency component data indicating a temperature change caused by the leaking gas, the second frequency component data indicating a background temperature change of the object to be monitored.

The image processing program for gas detection according to the third aspect of the present embodiment has the same operational effect as the image processing device for gas detection according to the first aspect of the present embodiment.

To describe the present invention, the present invention has been adequately and fully described above through the embodiment with reference to the drawings, but it should be appreciated that those skilled in the art can easily change and/or improve the embodiment described above. Therefore, unless modifications or refinements implemented by those skilled in the art are at the level of departing from the scope of the claims set forth in the appended claims, such modifications or refinements are interpreted as being included in the scope of the claims.

INDUSTRIAL APPLICABILITY

According to the present invention, it is possible to provide an image processing device for gas detection, an image processing method for gas detection, and an image processing program for gas detection.

The invention claimed is:

1. An image processing device for performing image processing on images obtained by shooting an object to be monitored at a plurality of time points, the image processing device comprising:
a hardware processor that performs a process of removing, from image data indicating the images, second frequency component data lower in frequency than first frequency component data indicating a luminance change of the object to be monitored, the second frequency component data indicating a background luminance change of the object to be monitored.

2. The image processing device according to claim 1, wherein the hardware processor performs a process of removing, from the image data, third frequency component data higher in frequency than the first frequency component data, the third frequency component data indicating high-frequency noise.

3. The image processing device according to claim 1, wherein
the image data is moving image data having a structure in which a plurality of frames is arranged on a time-series basis, and
the hardware processor defines, as time-series pixel data, data obtained by arranging pixel data of pixels at identical positions of the plurality of frames on a time-series basis, the hardware processor performing a process of removing the second frequency component data from each of a plurality of the time-series pixel data constituting the moving image data.

4. The image processing device according to claim 3, wherein the hardware processor:
defines, as the second frequency component data, data extracted by performing a first predetermined process on the time-series pixel data, the hardware processor extracting a plurality of the second frequency component data corresponding to each of the plurality of the time-series pixel data; and
defines, as first difference data, data obtained by calculating a difference between the time-series pixel data and the second frequency component data extracted from the time-series pixel data, the hardware processor calculating a plurality of the first difference data corresponding to each of the plurality of the time-series pixel data.

5. The image processing device according to claim 4, wherein the first predetermined process is a process of extracting the second frequency component data from the time-series pixel data by calculating a moving average of the time-series pixel data in units of a first predetermined number of the frames smaller than the plurality of frames.

6. The image processing device according to claim 4, wherein the hardware processor defines, as first fluctuation data, data indicating a fluctuation in the first difference data, the data being calculated by performing a predetermined operation on the first difference data in units of a second predetermined number of the frames, the hardware processor calculating a plurality of the first fluctuation data corresponding to each of the plurality of the time-series pixel data.

7. The image processing device according to claim 6, wherein the first fluctuation data is first variation data, and the hardware processor calculates the first variation data by calculating one of a moving standard deviation and moving dispersion of the first difference data in units of the second predetermined number of the frames smaller than the plurality of frames.

8. The image processing device according to claim 6, wherein the first fluctuation data is first absolute value addition data, the hardware processor defines, as first absolute value data, data indicating an absolute value of the first difference data obtained based on the first difference data, and the hardware processor calculates the first absolute value addition data by performing moving addition on the first absolute value data in units of the second predetermined number of the frames smaller than the plurality of frames.

9. The image processing device according to claim 6, wherein the hardware processor:

defines, as third frequency component data, data extracted by performing a second predetermined process on the time-series pixel data, the third frequency component data being data higher in frequency than the first frequency component data, the data indicating high-frequency noise, the hardware processor extracting a plurality of the third frequency component data corresponding to each of the plurality of the time-series pixel data;

defines, as second difference data, data obtained by calculating a difference between the time-series pixel data and the third frequency component data extracted from the time-series pixel data, the hardware processor calculating a plurality of the second difference data corresponding to each of the plurality of the time-series pixel data;

defines, as second fluctuation data, data indicating a fluctuation in the second difference data, the data being calculated by performing a predetermined operation on the second difference data in units of a fourth predetermined number of the frames, the hardware processor calculating a plurality of the second fluctuation data corresponding to each of the plurality of the time-series pixel data; and defines, as third difference data, data obtained by calculating a difference between the first fluctuation data and the second fluctuation data obtained from the same time-series pixel data, the hardware processor calculating a plurality of the third difference data corresponding to each of the plurality of the time-series pixel data.

10. The image processing device according to claim 9, wherein the second predetermined process is a process of extracting the third frequency component data from the time-series pixel data by calculating a moving average of the time-series pixel data in units of a third predetermined number of the frames.

11. The image processing device according to claim 9, wherein the second fluctuation data is second variation data, and the hardware processor calculates the second variation data by calculating one of a moving standard deviation and moving dispersion of the second difference data in units of the fourth predetermined number of the frames smaller than the plurality of frames.

12. The image processing device according to claim 9, wherein the second fluctuation data is second absolute value addition data, and the hardware processor defines, as second absolute value data, data indicating an absolute value of the second difference data, the data being obtained based on the second difference data, the hardware processor calculating the second absolute value addition data by performing moving addition on the second absolute value data in units of the fourth predetermined number of the frames smaller than the plurality of frames.

13. The image processing device according to claim 6, wherein the hardware processor:
defines, as third frequency component data, data higher in frequency than the first frequency component data, the data indicating high-frequency noise, the hardware processor defining, as second difference data, data obtained by calculating a weighted moving average of the time-series pixel data in units of a third predetermined number of the frames smaller than the plurality of frames by using a weighting coefficient that allows extraction of the third frequency component data, the second difference data being a difference between the time-series pixel data and the third frequency component data, the hardware processor calculating a plurality of the second difference data corresponding to each of the plurality of the time-series pixel data;

defines, as second fluctuation data, data indicating a fluctuation in the second difference data, the data being calculated by performing a predetermined operation on the second difference data in units of a fourth predetermined number of the frames, the hardware processor calculating a plurality of the second fluctuation data corresponding to each of the plurality of the time-series pixel data; and defines, as third difference data, data obtained by calculating a difference between the first fluctuation data and the second fluctuation data obtained from the same time-series pixel data, the hardware processor calculating a plurality of the third difference data corresponding to each of the plurality of the time-series pixel data.

14. The image processing device according to claim 3, wherein the hardware processor defines, as first difference data, data obtained by calculating a weighted moving average of the time-series pixel data in units of a first predetermined number of the frames smaller than the plurality of frames, by using a weighting coefficient that allows extraction of the second frequency component data, the first difference data being a difference between the time-series pixel data and the second frequency component data, and the hardware processor calculating a plurality of the first difference data corresponding to each of the plurality of the time-series pixel data.

15. The image processing device according to claim 3, wherein the hardware processor:
defines, as the first frequency component data, data extracted from the time-series pixel data by calculating a weighted moving average of the time-series pixel data in units of a predetermined number of the frames smaller than the plurality of frames by using a weighting coefficient that allows extraction of the first frequency component data, the hardware processor extracting a plurality of the first frequency component data corresponding to each of the plurality of the time-series pixel data; and defines, as fluctuation data, data indicating a fluctuation in the first frequency component, the data being obtained based on the first frequency component data, the hardware processor calculating a plurality of the fluctuation data corresponding to each of the plurality of the time-series pixel data.

16. The image processing device according to claim 3, wherein the hardware processor:
defines data obtained by performing Fourier transform on the time-series pixel data as Fourier transformed data, the hardware processor calculating a plurality of the Fourier transformed data corresponding to each of the plurality of the time-series pixel data;

defines, as specific frequency component cut data, data obtained by removing the second frequency component data from the Fourier transformed data, the hardware processor calculating a plurality of the specific frequency component cut data corresponding to each of the plurality of the time-series pixel data;

defines, as inverse Fourier transformed data, data obtained by performing inverse Fourier transform on the specific frequency component cut data, the hardware processor calculating a plurality of the inverse Fourier transformed data corresponding to each of the plurality of the time-series pixel data; and defines, as fluctuation data, data indicating a fluctuation in the inverse Fourier transformed data, the data being obtained based on the inverse Fourier transformed data, the hardware processor calculating a plurality of fluctuation data corresponding to each of the plurality of the inverse Fourier transformed data.

17. The image processing device according to claim 16, wherein the hardware processor defines, as the specific frequency component cut data, data obtained by removing, from the Fourier transformed data, third frequency component data that is higher in frequency than the first frequency component data and indicates high-frequency noise, and the second frequency component data, the hardware processor calculating the plurality of the specific frequency component cut data corresponding to each of the plurality of the time-series pixel data.

18. An image processing method comprising:
acquiring image data indicating images obtained by shooting an object to be monitored at a plurality of time points; and
performing a process of removing, from the image data, second frequency component data lower in frequency than first frequency component data indicating a luminance change of the object to be monitored, the second frequency component data indicating a background luminance change of the object to be monitored.

19. A non-transitory recording medium storing a computer readable image processing program for causing a computer to execute:
acquiring image data indicating images obtained by shooting an object to be monitored at a plurality of time points; and
performing a process of removing, from the image data, second frequency component data lower in frequency than first frequency component data indicating a luminance change of the object to be monitored, the second frequency component data indicating a background luminance change of the object to be monitored.

* * * * *